(12) United States Patent
Strair et al.

(10) Patent No.: US 6,576,622 B1
(45) Date of Patent: *Jun. 10, 2003

(54) DRUG COMBINATION FOR THE TREATMENT OF VIRAL DISEASES

(75) Inventors: Roger Strair, Skillman, NJ (US); Daniel Medina, Monmouth Junction, NJ (US); Peter Tung, New Haven, CT (US)

(73) Assignee: University of Medicine & Dentistry of New Jersey, Newark, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/929,249

(22) Filed: Sep. 10, 1997

Related U.S. Application Data

(63) Continuation-in-part of application No. 08/585,287, filed on Jan. 11, 1996, now abandoned, which is a continuation-in-part of application No. 08/403,320, filed on Mar. 14, 1995, now abandoned.

(51) Int. Cl.[7] ............................................... A61K 31/70
(52) U.S. Cl. .......................................... 514/50; 514/51
(58) Field of Search ...................................... 514/50, 51

(56) References Cited

U.S. PATENT DOCUMENTS 4,724,232 A * 2/1988 Rideout et al. ............... 514/50

OTHER PUBLICATIONS

Gao et al 122CA:394u, 1995.*
Nakai 111CA:167384a, 1989.*
Van Acrschot et al 111CA:58257R, 1989.*
Tortolani et al 120 CA 116622e, 1994.*

* cited by examiner

*Primary Examiner*—Russell Travers
(74) *Attorney, Agent, or Firm*—Perkins Coie LLP

(57) ABSTRACT

This invention pertains to a method for treating a human with human immunodeficiency virus infection which comprises administering to the human a therapeutically effective amount of a thymidine analog, which analog acts as an inhibitor of viral reverse transcriptase necessary for viral replication of human immunodeficiency virus, and a thymidylate synthase inhibitor, or pharmaceutically acceptable salts thereof.

11 Claims, 9 Drawing Sheets

DRUG COMBINATION FOR THE TREATMENT OF VIRAL DISEASES

BACKGROUND OF THE INVENTION

This application is a continuation-in-part application of application Ser. No. 08/585,287, filed Jan. 11, 1996, which application is a continuation-in-part application of parent application Ser. No. 08/403,320, filed Mar. 4, 1995 both abandoned.

FIELD OF THE INVENTION

The present invention relates to a method for treating a human with human immunodeficiency virus infection. The method comprises administering to the human a therapeutically effective amount of a thymidine analog, which analog acts as an inhibitor of viral reverse transcriptase necessary for viral replication of human immunodeficiency virus, and a thymidylate synthase inhibitor. In other embodiments, the method further comprises administering to the human a therapeutically effective amount of a folate antagonist or hydroxyurea, or both.

DESCRIPTION OF THE BACKGROUND

The disclosures referred to herein to illustrate the background of the invention and to provide additional detail with respect to its practice are incorporated herein by reference. For convenience, the disclosures are referenced in the following text and respectively grouped in the appended bibliography.

Sanctuary Growth of HIV in the Presence of AZT

Acquired immunodeficiency syndrome (AIDS) is believed to be caused by the human immunodeficiency virus (HIV). Human immunodeficiency virus is a retrovirus which replicates in a human host cell. The human immunodeficiency virus appears to preferentially attack helper T-cells (T-lymphocytes or OKT4-bearing T-cells). When the helper T-cells are invaded by the virus, the T-cells become a human immunodeficiency virus producer. The helper T-cells are quickly destroyed causing the B-cells and other T-cells, normally stimulated by helper T-cells, to no longer function normally or produce sufficient lymphokines and antibodies to destroy the invading virus or other invading microbes.

Although the human immunodeficiency virus does not necessarily cause death, the virus generally causes the immune system to be so depressed that the human develops secondary infections such as herpes, cytomegalovirus, pneumocystis carinni, toxoplasmosis, tuberculosis, other mycobacteria, and other opportunistic infections. Kaposi's sarcoma, lymphomas, and cervical cancer may also occur. Some humans infected with the human immunodeficiency virus appear to live with little or no symptoms, but appear to have persistent infections, while others suffer mild immune system depression with symptoms such as weight loss, malaise, fever, and swollen lymph nodes. These syndromes have been called persistent generalized lymphadenopathy syndrome (PGL) and AIDS related complex (ARC) and generally develop into AIDS. Humans infected with the AIDS virus are believed to be persistently infective to others.

Human immunodeficiency virus is an extremely heterogeneous virus. The clinical significance of this heterogeneity is evidenced by the ability of the virus to evade immunological pressure, survive drug selective pressure, and adapt to a variety of cell types and growth conditions. A comparison of isolates among infected patients has revealed significant diversity, and within a given patient, changes in the predominant isolate over time have been noted and characterized. In fact, each patient infected with human immunodeficiency virus harbors a "quasispecies" of virus with a multitude of undetected viral variants present and capable of responding to a broad range of selective pressures, such as those imposed by the immune system or antiviral drug therapy. Therefore, diversity is a major obstacle to pharmacologic or immunologic control of human immunodeficiency virus infection. Human immunodeficiency virus infection has multiple mechanisms to maximize its potential for genetic heterogeneity. These mechanisms result in an extremely diverse population of virus capable of responding to a broad range of selective pressures, including the immune system and antiretroviral therapy, with the outgrowth of genetically altered virus.

When a patient with human immunodeficiency virus infection is initiated on antiretroviral therapy, there is generally a virologic response characterized by declining viremia and antigenemia (5,7,19,20,25). Unfortunately, the currently available antiretroviral agents which have undergone clinical evaluation have only limited benefit because most patients will ultimately have evidence of worsening disease and increasing viral burden. This progression often occurs in association with the emergence of drug-resistant human immunodeficiency virus. For example, most patients who are treated with 3'-azido-3'-deoxythymidine (AZT) will have initial evidence, of improvement of clinical and laboratory parameters of human immunodeficiency virus infection (7,20). The duration of this benefit varies from patient to patient and is likely to be disease stage related (21). Ultimately, however, most patients will have progressive disease and genotypic or phenotypic evidence of the appearance of AZT-resistant human immunodeficiency virus (9,12). Since clinical failure and the appearance of virus with high level resistance to AZT both occur with evidence of increasing levels of viremia and changes in viral tropism, it has been difficult to ascribe the clinical failure solely to the development of AZT resistance (2,11). Nevertheless, it seems likely that AZT resistance ultimately contributes to the clinical failure seen in most patients receiving prolonged AZT therapy.

While the development of viral-encoded drug resistance may contribute to the limited efficacy of currently used antiretroviral agents, it cannot explain all of the in vitro and in vivo phenomena associated with viral replication in the presence of an antiretroviral agent. For example, many patients will have continued evidence of viral replication after initiation of AZT therapy, but the isolated virus will remain sensitive to AZT when analyzed in tissue culture (7,20). In contrast, high level human immunodeficiency virus resistance to many of the non-nucleoside reverse transcriptase inhibitors develops very rapidly in culture and in patients (13,16,22,23). Some of these differences may relate to the complexity and prevalence of viral variants harboring pre-existing drug resistance mutations prior to the application of the selective pressure. However, some of the differences may be due to cellular heterogeneity in the uptake or metabolism of the antiretroviral agents, that is, each cell population may have some cells that are refractory to the antiviral effects of the drug. This would allow a subset of the cellular population to be successfully infected by genetically drug-sensitive human immunodeficiency virus in the presence of the antiviral drug. Depending upon the prevalence of drug-resistant human immunodeficiency virus in the initial population, the relative rates of replication of drug-resistant and drug-sensitive virus, and the percentage of cells refractory to the antiviral effects of the drug, different patterns of viral breakthrough would emerge. Notably, the non-nucleoside reverse transcriptase inhibitors do not undergo cellular metabolism and cellular effects of uptake or metabolism may be less likely in this setting. This is consistent with the observation that viral-encoded drug resistance to the non-nucleoside reverse transcriptase inhibitors develops very rapidly under selection in tissue culture and in patients. In fact, the rapid, development of resistance in patients suggests that the blood and plasma compartment of virus is subjected to drug selective pressure. The presence of human immunodeficiency virus, but lack of AZT-resistant human immunodeficiency virus, early after the initiation of AZT suggests that a component of this viral pool may be capable of averting selective drug pressure in vivo. Continued viral replication in cells in which, AZT is an ineffective antiretroviral agent could conceivably result in the continued growth of virus that is sensitive to AZT. An increase in the number of these cells over time could also alter viral growth kinetics in the presence of AZT without the emergence of virus with high level AZT resistance. Therefore, many mechanisms may contribute to the inability of an antiviral agent to completely suppress human immunodeficiency virus infection. Viral growth in the presence of the non-nucleoside reverse transcriptase inhibitors appears due to the rapid selection of genetically resistant virus. In contrast, genetic viral drug resistance does not appear to be the major mechanism contributing to early viral growth in the presence of AZT.

The use of recombinant human immunodeficiency virus encoding reporter genes has been reported to analyze viral breakthrough infection in the presence of antiretroviral agents (26). In that study, to determine the prevalence of viral variants spontaneously resistant to the non-nucleoside reverse transcriptase inhibitor TIBO R82150, HeLa-T4 cells were infected in the presence of drug with replication defective HIV-gpt (18,26) or HIV-LacZ (26). The recombinant virus used for these infections was produced by infection of cell lines containing an integrated copy of the defective recombinant virus with replication-competent human immunodeficiency virus. The replication-competent human immunodeficiency virus provided the necessary gene products to rescue the defective virus. The prevalence of viral variants containing mutations encoding resistance to TIBO R82150 was reflected by the prevalence of recombinant viruses capable of infecting HeLa-T4 cells in the presence of TIBO R82150. The presence of reporter genes in the recombinant viruses allowed for a quantitative analysis of a single cycle of infection on a single cell basis.

U.S. Pat. No. 4,724,232 (Rideout et al.) discloses a method for treating a human having acquired immunodeficiency syndrome which comprises administering to the human 3'-azido-3'-deoxythymidine.

Cancer, Dec. 15, 1992, vol. 70, No. 12, pp. 2929–2934 (Posner et al.) discloses the use of 3'-azido-3'-deoxythymidine and 5-fluorouracil in the treatment of cancer.

Early HIV Breakthrough Infection in the Presence of Stavudine

The measurement of plasma HIV RNA copy number after the initiation of antiviral therapy has provided several insights into the kinetics and dynamics of HIV infection. Initial studies quantitating HIV RNA after the initiation of a non-nucleoside reverse transcriptase inhibitor (NNRTI), nevirapine, indicated a very rapid turnover of plasma HIV (28). In those studies there was an initial decline in HIV RNA followed by a rapid increase in plasma viral RNA. The studies with nevirapine demonstrated that the rapid rebound in HIV RNA levels was a consequence of the outgrowth of HIV with, phenotypic and genotypic resistance to nevirapine (28). An in vitro model of HIV infection after the initiation of a different NNRTI (TIBO) has also indicated a similarly high prevalence of variants capable of infection in the presence of the drug (26).

Similar clinical and laboratory studies analyzing early HIV infection in the presence of AZT have also been undertaken (29). In contrast to the clinical studies with nevirapine, early HIV infection in the presence of AZT does not appear to be predominated by the early outgrowth of drug-resistant HIV. While the amount of virus circulating in plasma shortly after the initiation of AZT rapidly declines, the remaining circulating virus after this decline does not contain mutations known to encode resistance to AZT (29). Laboratory infections using an in vitro model of infection in the presence of AZT have demonstrated a similar pattern: early breakthrough infection independent of the presence of genetic resistance (31). These more complex dynamics may be a consequence of a variety of pharmacologic, cellular and viral features. The mutations associated with AZT-resistance may be present in the initial (unselected) viral population but mutant HIV with high level AZT-resistance generally contain multiple mutations associated with AZT-resistance and the emergence of these variants often occurs over months-years. While the slow emergence of these high level resistant variants can be explained by a low prevalence of AZT-resistant variants, the need for superimposed mutations, or selection against the emergence of these variants, the early outgrowth of AZT-sensitive virus in the presence of AZT must be explained by virologic, cellular or pharmacologic features that result in the ability of HIV-1 that is genotypically and phenotypically sensitive to AZT to replicate in the presence of AZT.

A quantitative in vitro model of HIV infection which utilizes recombinant HIV has been used to characterize some of the mechanisms responsible for HIV kinetics after the initiation of antiviral drugs (26,31). In that model a replication-defective HIV encoding a selectable marker is used to assess a single cycle of infection in the absence of either repeated cycles of infection or selection of virus in the presence of antiviral drugs. The use of a replication-defective virus allows an assessment of mechanisms of early HIV breakthrough infection in the presence of antiviral drugs and has been used to quantitate HIV breakthrough infection. Similarly, this system has been used to determine that such infection in the presence of a NNRTI is likely due to infection by genetically resistant virus while early infection in the presence of AZT is due to the infection by virus without genetic drug resistance (26,31). These in vitro results mimic those described in clinical studies of HIV dynamics after the initiation of a NNRTI (28) or AZT (29).

Another feature of the replication-defective recombinant HIV system is that cells infected with HIV in the presence of the antiviral drug can be readily isolated and characterized. Using this approach it has been possible to determine that some of the cells infected in the presence of AZT had metabolic features that rendered AZT an ineffective antiviral drug. Attempts to reverse these metabolic features has resulted in the development of new drug combinations designed to modulate the antiviral efficacy of AZT. One such combination has improved antiviral efficacy in both cells demonstrated to be refractory to the antiviral effects of AZT and primary blood mononuclear cells (35).

SUMMARY OF THE INVENTION

Figure 1:
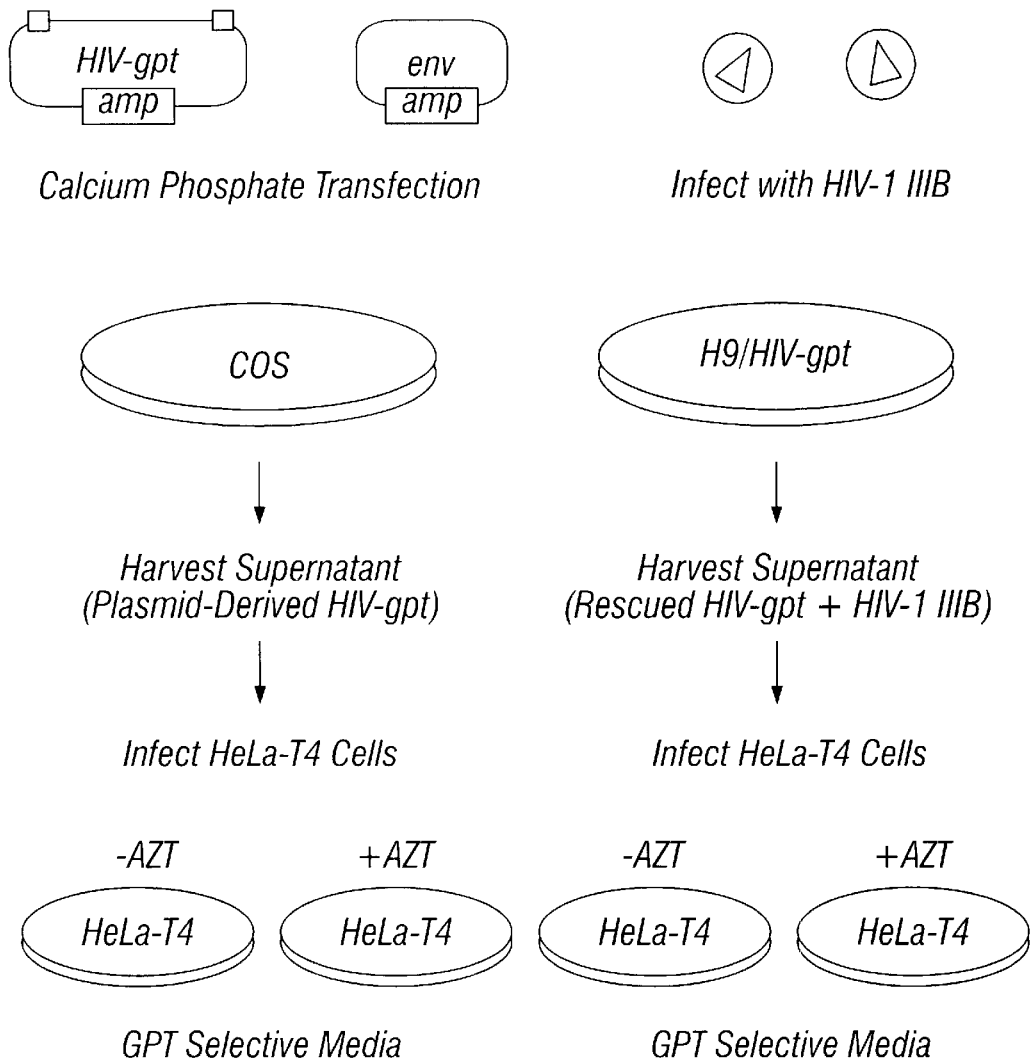
FIG. 1 is a schematic representation of the production of recombinant HIV-gpt by COS cell transfection or rescue from the H9/HIV-gpt cell line.

This invention pertains to a method for treating a human with human immunodeficiency virus infection (acquired immunodeficiency syndrome) which comprises administering to the human a therapeutically effective amount of a thymidine analog, which analog acts as an inhibitor of viral reverse transcriptase necessary for viral replication of human immunodeficiency virus, and a thymidylate synthase inhibitor, or pharmaceutically acceptable salts thereof. In other embodiments, the method further comprises administering to the human a therapeutically effective amount of a folate antagonist or hydroxyurea, or both.

DETAILED DESCRIPTION OF THE INVENTION

Sanctuary Growth of HIV in the Presence of AZT

Human immunodeficiency virus resistance to the non-nucleoside reverse transcriptase inhibitors emerges very rapidly under selection in culture and in patients. In contrast, AZT-resistant HIV generally emerges in patients only after more prolonged therapy. Although HIV can be cultured from many patients shortly after the initiation of AZT treatment, characterization of the virus that is cultured generally indicates that it is sensitive to AZT. To initiate an evaluation of the mechanisms contributing to early HIV breakthrough in the presence of AZT and other nucleoside analogs, replication-defective HIV encoding reporter genes were utilized. These recombinant HIV allow a quantitative analysis of a single cycle of infection. Results with these defective HIV indicate that early infection in the presence of AZT often results from the infection of a cell which is refractory to the antiretroviral effects of AZT. Characterization of cell lines derived from such infected cells has demonstrated decreased accumulation of AZT, increased phosphorylation of thymidine to TTP, and increased levels of thymidine kinase activity. In addition, AZT inhibition of replication-competent HIV infection is also significantly impaired in this cell line.

Early HIV Breakthrough Infection in the Presence of Stavudine

By utilizing replication-defective HIV encoding reporter genes, applicants have demonstrated that early HIV breakthrough infection in the presence of Stavudine results from infection of cells which are refractory to the antiviral effects of the drug. In addition, applicants demonstrate that the combination of Stavudine and Floxuridine has potent antiviral activity in cells refractory to the antiviral activity of Stavudine alone. Data is presented indicating that the predominant mechanism of HIV breakthrough early after the initiation of stavudine (d4T) is related to the inefficacy of d4T as an antiviral agent in a subset of the host population. This inefficacy is demonstrated to be independent of the presence of HIV with genetic drug resistance and has also been demonstrated in several cell types and with retroviruses other than HIV. These results may help explain several features of the in vivo and in vitro selection of d4T resistant virus and, contribute to an understanding of the mechanisms responsible for HIV kinetics after the initiation of antiviral drugs.

The present invention relates to a method for treating a human with human immunodeficiency virus infection. The method comprises administering to the human a therapeutically effective amount of a thymidine analog, which analog acts as an inhibitor of viral reverse transcriptase necessary for viral replication of human immunodeficiency virus, and a thymidylate synthase inhibitor. Thymidine analogs, such as 3'-azido-3'-deoxythymidine (AZT), are prodrugs in the treatment of acquired immunodeficiency syndrome. 3'-Azido-3'-deoxythymidine is converted by cellular enzymes to 3'-azido-3'-deoxythymidine monophosphate (AZTMP). The monophosphate is then converted by cellular enzymes to 3'-azido-3'-deoxythymidine diphosphate (AZTDP) and 3'-azido-3'-deoxythymidine triphosphate (AZTTP). In human cells infected with HIV, 3'-azido-3'-deoxythymidine triphosphate is an inhibitor of the viral reverse transcriptase necessary for viral replication. Some cells, however do not efficiently metabolize AZT to the triphosphate and may overproduce the natural thymidine triphosphate, which competes with the antiviral activity of AZTTP. Studies have demonstrated that these cells contribute to the early failure of the antiviral activity of AZT. By coadministering a thymidylate synthase inhibitor with the thymidine analog, applicants have found that that the thymidine analog is a more effective inhibitor of HIV replication. The thymidylate synthase inhibitor may function by resulting in lower levels of thymidine triphosphate to compete with the phosphorylated thymidine analog reverse transcriptase inhibition.

In another embodiment, the method further comprises administering to the human a therapeutically effective amount of a folate antagonist together with the thymidine analog and the thymidylate synthase inhibitor to modulate the effects of the thymidine analog. In yet another embodiment, the method further comprises administering to the human a therapeutically effective amount of hydroxyurea together with the thymidine analog and the thymidylate synthase inhibitor to modulate the effects of the thymidylate synthase inhibitor. In still yet another embodiment, both the folate antagonist and hydroxyurea may be administered with the thymidine analog and the thymidylate synthase inhibitor.

Use of Floxuridine to Modulate the Antiviral Activity of AZT

Recent clinical studies have demonstrated that early HIV replication after initiation of AZT is generally a consequence of the replication of AZT-sensitive virus (29). A prior in vitro analysis of this early breakthrough replication in the presence of AZT has demonstrated the infection of cells in which AZT was an ineffective antiviral agent (31). A metabolic characterization of these cells has led to the development of a novel combination therapy designed to potentiate the antiviral efficacy of AZT. The present invention describes the antiviral effects of the combination of floxuridine and AZT. This combination suppresses early viral breakthrough, lowers the $IC_{50}$ of AZT, and has particular antiviral efficacy in the subset of cells that are infected with AZT-sensitive virus in the presence of AZT. The antiviral efficacy of this combination in peripheral blood mononuclear cells suggests potential clinical utility.

In an attempt to explain the ability of genetically-sensitive HIV to replicate in the presence of AZT, applicants have initially utilized recombinant replication-defective HIV to quantitate infection in the presence of AZT (31). In those studies, replication-defective HIV encoding a selectable marker was used to infect target cells in the presence of 10 $\mu$M AZT. The cells infected with the defective HIV were isolated by expression of the selectable marker. A subset of these infected cells was demonstrated to be readily infected with another HIV in the presence of 10 $\mu$M AZT. These cells were persistently refractory to the antiviral effects of AZT and were demonstrated to have excessive phosphorylation of thymidine to TTP, increased thymidine kinase activity and decreased accumulation of AZTTP.

These data suggested that a component of early infection with AZT-sensitive HIV in the presence of AZT was a consequence of the infection of cells which were refractory to the antiviral effects of AZT. Some of these cells had metabolic factors resulting in reduced AZTTP/TTP ratios in the cells. These data also suggest that it may be possible to overcome this reduced antiviral efficacy of AZT by biochemical modulation of TTP pool sizes. One way to potentially modulate these cells is with fluoropyrimidines such as 5-fluorodeoxyuridine (FUdR). These compounds are known to reduce cellular thymidine pools by the inhibition of thymidylate synthase.

In the present invention, applicants demonstrate the suppression of early HIV infection in the presence of AZT with FUdR. FUdR will be shown to potentiate the antiviral effects of AZT in whole cell populations (including peripheral blood mononuclear cells [PBMC]) as well as in subsets of. cells isolated by infection with recombinant HIV in the presence of AZT. Infection of these latter cells will be shown to be extremely sensitive to combined AZT-FUdR therapy.

The term "prodrug", as used herein refers to compounds which undergo biotransformation prior to exhibiting their pharmacological effects. The chemical modification of drugs to overcome pharmaceutical problems has also been termed "drug latentiation." Drug latentiation is the chemical modification of a biologically, active compound to form a new compound which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances which are converted after administration to the actual substance which combines with receptors. The term prodrug is a generic term for agents which undergo biotransformation prior to exhibiting their pharmacological actions.

As set out above, the present invention relates to a method for treating a human with human immunodeficiency virus infection which comprises administering to the human a therapeutically effective amount of a thymidine analog, which analog acts as an inhibitor of viral reverse transcriptase necessary for viral replication of human immunodeficiency virus, and a thymidylate synthase inhibitor.

The thymidine analogs, and prodrugs thereof, which may be employed in the present invention are compounds which act as inhibitors of viral reverse transcriptase necessary for viral replication of human immunodeficiency virus. In general, the thymidine analogs are prodrugs which are converted by cellular enzymes to their respective active monophosphates, diphosphates, and/or triphosphates which are inhibitors of viral reverse transcriptase. Nonlimiting examples of thymidine analogs may be selected from the group consisting of 3'-azido-3'-deoxythymidine, and D4T. In a preferred embodiment, the thymidine analog is 3'-azido-3'-deoxythymidine.

3'-Azido-3'-deoxythymidine (AZT, azidothymidine, zidovudine, Retrovir™), is an antiretroviral drug active against human immunodeficiency virus. 3'-Azido-3'-deoxythymidine is an inhibitor of the replication of retroviruses including HIV also known as HTLV 111, LAV, or ARV. 3'-Azido-3'-deoxythymidine is a thymidine analog in which the 3'-hydroxy (—OH), group of thymidine is replaced by an azido (—$N_3$) group. Cellular thymidine kinase converts 3'-azido-3'-deoxythymidine into AZT monophosphate. The monophosphate is further converted into AZT diphosphate by cellular thymidylate kinase and to the AZT triphosphate derivative by other cellular enzymes. 3'-Azido-3'-deoxythymidine triphosphate interferes with the HIV viral RNA dependent DNA polymerase (reverse transcriptase) and thus, inhibits viral replication. 3'-Azido-3'-deoxythymidine is useful in treating humans identified as having HIV infection. 3'-Azido-3'-deoxythymidine is disclosed in J. R. Horwitz et al., J. Org. Chem. 29, July 1964, pp. 2076–2078; M. Imazawa et al., J. Org. Chem., 43(15) 1978, pp. 3044–3048; also see Biochemical Pharmacology, Vol. 29, pp. 1849–1851; C. J. Kreig et al., Experimental Cell Research 116 (1978) pp. 21–29; W. Ostertag et al, Proc. Nat. Acad. Sci. U.S.A. 71 (1974).

The thymidine analogs which act as an inhibitor of viral reverse transcriptase necessary for viral replication of human immunodeficiency virus, may be administered as the free base or in the form of a pharmaceutically acceptable salt, e.g., an alkali metal salt such as sodium or potassium, an alkaline earth salt or an ammonium salt (all of which are hereinafter referred to as a pharmaceutically acceptable base salt). The salts of the thymidine analog are converted to the free base after being administered to the human and are thus prodrugs.

The amount of thymidine analog which acts as an inhibitor of viral reverse transcriptase present in the therapeutic compositions of the present invention is a therapeutically effective amount. A therapeutically effective amount of thymidine analog is that amount necessary to inhibit viral reverse transcriptase. All prodrugs or precursors are administered to a human in a therapeutically effective amount sufficient to generate an effective amount of the compound which inhibits viral reverse transcriptase necessary for viral replication of human immunodeficiency virus. In general, a suitable effective dose of the thymidine analog or its pharmaceutically acceptable basic salts will be in the range of about 5 mg to 250 mg per kilogram body weight of recipient per day, preferably in the range of 7.5 mg to 100 mg per kilogram body weight per day, and most preferably in the range 10 mg to 40 mg per kilogram body weight per day.

The thymidylate synthase inhibitors, and prodrugs thereof, which may be employed in the present invention are compounds which are antimetabolites which interfere with the synthesis of deoxyribonucleic acid (DNA) and to a lesser extent inhibit the formation of ribonucleic acid (RNA). In general, the thymidylate synthase inhibitors inhibit the synthesis of, thymidine triphosphate so that the phosphorylated thymidine analog which acts as an inhibitor of the viral reverse transcriptase can compete more effectively with thymidine triphosphate and will more effectively inhibit viral reverse transcriptase necessary for viral replication of human immunodeficiency virus. Nonlimiting examples of thymidylate synthase inhibitors may be selected from the group consisting of 5-fluorouracil, 5-fluoro-2-pyrimidone (a prodrug of 5-fluorouracil), and floxuridine. Preferably, the thymidylate synthase inhibitor is floxuridine. These drugs may inhibit HIV infection by other mechanisms as well.

5-Fluorouracil (5-FU) is a fluorinated pyrimidine antineoplastic antimetabolite. The metabolism of 5-fluorouracil in the anabolic pathway blocks the methylation reaction of deoxyuridylic acid to thymidylic acid and interferes with the synthesis of deoxyribonucleic acid (DNA) and to a lesser extent inhibits the formation of ribonucleic acid (RNA). Since DNA and RNA are essential for cell division and growth, the effect of fluorouracil may be to create a thymine deficiency which provokes unbalanced growth and death of the cell. The effects of DNA and RNA deprivation are most marked on those cells which grow more rapidly and which take up fluorouracil at a more rapid pace.

Floxuridine (FUdr) is a fluorinated pyrimidine antineoplastic antimetabolite. Chemically, floxuridine is 2'-deoxy-5-fluorouridine. FUdr produces the same toxic and antimetabolic effects as does 5-fluorouracil. The primary effect is to interfere with the synthesis of deoxyribonucleic acid (DNA) and to a lesser extent inhibit the formation of ribonucleic acid (RNA). Derivatives of 5-fluorouracil and floxuridine may also be incorporated into DNA or RNA.

The amount of thymidylate synthase inhibitor present in the therapeutic compositions of the present invention is a therapeutically effective amount. A therapeutically effective amount of thymidylate synthase inhibitor is that amount necessary to improve the antiviral efficacy of the thymidine analog so that the phosphorylated thymidine analog which acts as an inhibitor of the viral reverse transcriptase can compete more effectively in the inhibition of viral reverse transcriptase necessary for the replication of HIV. In general, a suitable effective dose of the thymidylate synthase inhibitor or its pharmaceutically acceptable salts will be in the range of about 0.01 mg to 25 mg per kilogram body weight of recipient per day, preferably in the range of 0.01 mg to 10 mg per kilogram body weight per day, and most preferably in the range 0.01 mg to 5 mg per kilogram body weight per day.

As set out above, the method of the present invention may further comprise administering to a human a therapeutically effective amount of a folate antagonist together with the thymidine analog which acts as an inhibitor of viral reverse transcriptase and the thymidylate synthase inhibitor to modulate the effects of the thymidine analog. The folate antagonists, and prodrugs thereof, which may be employed in the present invention are compounds which are antimetabolites which interfere with the synthesis of deoxyribonucleic acid (DNA) and to a lesser extent inhibit the formation of ribonucleic acid (RNA). Nonlimiting examples of folate antagonists may be selected from the group consisting of methotrexate and trimetraexate. Preferably, the folate antagonist is methotrexate.

Methotrexate (Amethopterin) is an antimetabolite used in the treatment of certain neoplastic diseases, severe psoriasis, and adult rheumatoid arthritis. Chemically methotrexate is N-[4-[[(2,4-diamino-6-pteridinyl)-methyl]methylamino] benzoyl]-L-glutamic acid. Methotrexate inhibits dihydrofolic acid reductase. Dihydrofolates must be reduced to tetrahydrofolates by this enzyme before they can be utilized as carriers of one carbon groups in the synthesis of purine nucleotides and thymidylate. Therefore, methotrexate interferes with DNA synthesis, repair, and cellular replication.

The amount of folate antagonist present in the therapeutic compositions of the present invention is a therapeutically effective amount. A therapeutically effective amount of folate antagonist is that amount necessary to modulate the effects of the thymidine analog. In general, a suitable effective dose of folate antagonist or its pharmaceutically acceptable salts will be in the range of about 0.05 mg to 25 mg per kilogram body weight of recipient per day, preferably in the range of 0.05 mg to 10 mg per kilogram body weight per day, and most preferably in the range of 0.05 mg to 4 mg per kilogram body weight per day.

As set out above, the method of the present invention may further comprise administering to a human a therapeutically effective amount of hydroxyurea, and prodrugs thereof, together with the thymidine analog and the thymidylate synthase inhibitor to modulate the effects of the thymidylate synthase inhibitor. Hydroxyurea has the structural formula $H_2N$—CO—NHOH. The precise mechanism by which hydroxyurea produces cytotoxic effects is not known but it is believed that hydroxyurea causes an immediate inhibition of DNA synthesis without interfering with the synthesis of ribonucleic acid or of protein.

The amount of hydroxyurea present in the therapeutic compositions of the present invention is a therapeutically effective amount. A therapeutically effective amount of hydroxyurea is that amount necessary to modulate the effects of the thymidylate synthase inhibitor. In general, a suitable effective dose of hydroxyurea or its pharmaceutically acceptable salts will be in the range of about 5 mg to 250 mg per kilogram body weight of recipient per day, preferably in the range of 7.5 mg to 100 mg per kilogram body weight per day, and most preferably in the range 10 mg to 40 mg per kilogram body weight per day.

Administration may be by any suitable route including oral, rectal, nasal, topical (including buccal and sublingual), vaginal, and parenteral (including subcutaneous, intramuscular, intravenous and intradermal), with oral or parenteral being preferred. The preferred route may vary with the condition and age of the recipient.

While it is possible for the administered ingredients to be administered alone, it is preferable to present them as part of a pharmaceutical formulation. The formulations of the present invention comprise the administered ingredients, as above defined, together with one or more acceptable carriers thereof and optionally other therapeutic ingredients. The carrier(s) must be "acceptable" in the sense of being compatible with the other ingredients of the formulation and not deleterious to the recipient.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and may be prepared by any methods well known in the art of pharmacy.

Such methods include the step of mixing the ingredients to be administered with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets, or tablets each containing a predetermined amount of the active ingredient; as a powder or granules; as a solution or a suspension.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surfactant or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising the ingredients in a flavored base, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered and a pharmaceutically acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous, or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, buffers bacteriostats and solutes which render the formulation isotonic with the blood of the intended recipient; and aqueous and non-aqueous sterile suspensions which may include suspending agents and thickening agents.

The formulations may be presented in unit dose or multidose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, or an appropriate fraction thereof, of the administered ingredient.

The present invention is further illustrated by the following examples which are presented for purposes of demonstrating, but not limiting, the preparation of the compounds and compositions of this invention.

EXAMPLES

Sanctuary Growth of HIV in the Presence of AZT
Methods
Construction of Recombinant Proviral DNA The HIV construct encoding LacZ has been described (26). It contains the LacZ gene driven by an SV40 promoter inserted into a large deletion in the HIV genome extending from the 5' end of the pol gene to the 3' end of the env gene. The HIV-gpt and HXB2env plasmids were kindly provided by Kathleen Page (University of California, San Francisco, Calif.) (18). The HIV-gpt plasmid contains an HXB2 provirus into which an SV40 promoter gpt (E. coli guanine phosphoribosyl transferase) gene was inserted into the env region. The HXB2 env plasmid contains the HXB2 gpl60 gene driven by an SV40 promoter.

Production of "Plasmid Derived" Recombinant Retroviruses

All transfections and cell culture were performed in an approved facility using BSL3 techniques. Plasmid DNA co-transfections into COS cells were performed as described by Page et al. (18). Supernatants from COS cells were collected 40 hours after transfection and assayed for infectious recombinant HIV-LacZ virus by inoculating $2 \times 10^5$ HeLa-T4 cells with 0.1 ml of filtered (0.45 $\mu$m) supernatant. Cells were stained for beta-galactosidase activity with X-gal 48 hours after infection as described (26,27). To assay for infectious recombinant HIV-gpt virus, the infected cells were split 1:10 into gpt selective media as described (26). Medium changes were performed every 3 days and colonies were counted 10–14 days post-infection after staining with 1% crystal violet in 10% formalin.

Cell Lines Containing Defective HIV-gpt and HIV-LacZ

The H9/HIV-gpt cell line and HeLa T4/HIV-LacZ cell line were prepared and used as previously described (26). Rescue of defective retroviruses from the H9/HIV-gpt cell line and the HeLa T4/HIV-LacZ cell line were performed as previously described (26). Following each rescue infection, the resultant titer of HIV-LacZ or HIV-gpt was determined and the inoculum used to infect HeLa-T4 cells was adjusted depending upon the number of infectious events to be analyzed.

HPLC Analysis of Clones

Cell lines were incubated with $^3$H-thymidine or $^3$H-AZT for 4 hours. Dried methanol extracts of the clones were redissolved in 60 μof distilled water and centrifuged to remove undissolved material. Twenty microliters of the sample was injected and separated on a 10×100 mm Rainin Hydropore anion exchange column. The nucleosides were eluted from the column with a linear gradient of potassium phosphate (5 mM to 1 M, pH4.0) at a flow rate of 1 ml/min. The samples were collected (0.5 ml), mixed with 5 ml Packard scintillation fluid, and quantitated using a liquid scintillation counter. Phosphorylated derivatives of thymidine and AZT were identified with authentic standards.

Cytotoxicity Assay

AZT-mediated cytotoxicity was assayed in cells persistently refractory to the antiviral effects of AZT (R116) and in cells sensitive to the antiviral effects of AZT (HT4, S pool and S1) using a standard assay (14). Triplicate wells of 24-well plates containing $3\times10^4$ cells were cultured in the absence or presence of various concentrations of AZT. Three days later, drug cytotoxicity was quantitated with a standard MTT assay in which the uptake and metabolism of 3-[4,5-dimethylthiazol-2-yl]2,5-dephenyltetrazolium bromide (MTT) by cells was measured (14). The amount of formazan produced in 2 hours was determined by dissolving the product in 100% DMSO and then measuring the absorbance at 570 nm.

Northern Blot Analysis

Total RNA from S1 and R116 cells were extracted as described previously (4). Equal amounts of total RNAs were electrophoresed on an agarose gel containing 1% formaldehyde and blotted onto a nylon membrane. The RNAs were hybridized with a $^{32}$P-labled human thymidine kinase probe (3). The labeled bands were visualized using autoradiography and quantitated using a Molecular Dynamics Personal Densitometer.

Thymidine Kinase Assay

Thymidine kinase activity was determined in cell lines sensitive and resistant to AZT. Cellular extracts of S1 and R116 cells were prepared according to Sherley and Kelly (24) and assayed for thymidine kinase activity as described by Lee and Cheng (10). Protein concentration of each extract was determined using Biorad Protein Reagent.

Use of Floxuridine to Modulate the Antiviral Activity of AZT

Materials and Methods

Cells

Cell line R116 is a derivative of HeLa-T4 cells that was isolated after infection of HeLa-T4 cells with HIV-gpt in the presence of 10 ∞M AZT (31). This cell line was demonstrated to be refractory to the antiviral effects of AZT by virtue of reinfection with either recombinant or replication-competent HIV infection in the presence of AZT. Cell line S1 is a derivative of HeLa-T4 cells that was isolated after infection of HeLa-T4 cells with HIV-gpt in the absence of AZT (31). Cells were cultured in Dulbecco's modified Eagle's medium supplemented with antibiotics, 2 mM L-glutamine, and 10% fetal bovine serum (FBS). H9 cells, JE6.1 cells and MT-2 cells were cultured in RPMI 1640 medium supplemented with antibiotics, 2 mM L-glutamine, and 10% FBS. Peripheral blood mononuclear cells (PBMC) isolated from healthy HIV-1 seronegative donors were activated with PHA (10 ug/ml) for 72 hours prior to HIV-1 infection. PBMC were maintained in RPMI 1640 supplemented with 10% interleukin-2 (Advanced Biotechnologies, Columbia, Md.), 20% FBS, 2 mM L-glutamine and antibiotics.

Virus

Stock preparations of HIV-1 IIIB were harvested from H9 cells by the "shake off method" (13). An AZT sensitive clinical isolate (HIV-1$_{preAOS}$) (9) was prepared in MT-2 cells. Stock virus infectivity was determined by end-point dilution in MT-2 cells (32). Virus-induced cytopathic effect (syncytium formation) was scored 7 days post-infection and the TCID$_{50}$ was calculated with the Reed and Muench equation (33).

Compounds

Azidothymidine (AZT) and Floxuridine (FUdR) were purchased from Sigma Chemical Co. (St. Louis, Mo.) and were dissolved in phosphate buffered saline, sterile filtered (0.22 um) and stored at −20° C.

HIV RT Assay

HIV-1 production in infected, cultures was determined by a $^{32}$P-based assay as described (34). RT activity was determined by qualification of $^{32}$P bound to the DE81 paper by using a Molecular Dynamics phosphorimager. The results are reported as pixel units per microliter of the reaction mixture.

Cytotoxicity Assay

A checkerboard analysis of the cytotoxicity of AZT and FUdR alone and in combination was assayed. Triplicate wells of of 24-well plates containing $1\times10^5$ cells were cultured in the absence or presence of various concentrations of each drug alone and in combination. Samples were taken every two days for 8–10 days. Drug cytotoxicity was quantitated by the MTT reduction assay (14). The amount of formazan produced in 4 hours was determined by dissolving the product in 0.1N HCl made with 2-propanol and then measuring the A$_{570}$.

Early HIV Breakthrough Infection in the Presence of Stavudine

Materials and Methods

Cells

The lymphoid cell lines H9 and JE6.1 were cultured in RPMI 1640 medium supplemented with antibiotics, 2 mM L-glutamine and 10% FBS. Peripheral blood mononuclear cells (PBMC) isolated from healthy HIV-1 seronegative donors were activated with PHA (10 ug/ml) for 72 hours prior to infection. After PHA stimulation, PBMCs were maintained in RPMI 1640 supplemented with 10% interleukin-2 (Advanced Biotechnologies, Columbus, Md.), 20% FBS, 2mM L-glutamine and antibiotics.

Virus

Production of recombinant HIV-gpt has been described elsewhere (26). The amphotropic cell line PA317 was transfected with the recombinant murine retrovirus pLXSN (36) and was used as the source of the recombinant MLV-neo virus. Stock preparations of HIV-1IIIB were harvested from H9 cells by the "shake off method" (13). Stock virus infectivity was determined by end-point dilution in MT-2 cells (32). Virus induced cytopathic effect was scored 7 days post-infection and the TCID50 was calculated with the Reed and Muench equation (33).

Compounds

Stavudine (D4T) and Floxuridine (FUdr) were purchased from Sigma Chemical Co. (St. Louis, Mo.) and were dissolved in phosphate buffered saline, sterile filtered and stored at −20° C.

HIV-1 RT Assay

HIV-1 production in infected cells was determined by a 32P-based assay as described (37). RT activity was determined by quantification of 32P-bound to DE81 paper by using a Molecular Dynamics phosphorimager. The results are reported as pixel units per microliter of the reaction mixture.

Cytotoxicity Assay

A checkerboard analysis of the cytotoxicity of D4T and FUdr alone and in combination was assayed. Triplicate wells of 24 well plates containing 1×105 cells were cultured in the absence or presence of various concentrations of each drug alone or in combination. Samples were taken every two days for 8–10 days. Drug cytotoxicity was quantitated by the MTT reduction assay (14). The amount of formazan produced in 4 hours was determined by dissolving the product in 0.1N HCL made with 2-propanol and the measuring the A570.

Results

Sanctuary Growth of HIV in the Presence of AZT

HIV-gpt Infection of Cells in the Absence and Presence of AZT

HeLa-T4 cells were infected with a recombinant HIV, HIV-gpt, in the presence or absence of 10 $\mu$M AZT (FIG. 1). Two separate populations of HIV-gpt were utilized for these infections. One population of HIV-gpt was produced in COS cells by co-transfection of the HIV-gpt plasmid with a plasmid encoding the HXB2 env gene. The infectious virions produced by this co-transfection have little genetic diversity in that they are produced from products encoded by plasmids in COS cells. The second population of HIV-gpt was genetically more diverse, being produced by rescue from the H9/HIV-gpt cell line with replication competent HIV-1IIIB that had been propagated in culture (26). After infection, the HeLa-T4 cells were placed in gpt selective media and the number of colonies developing by day 10 was used as an indicator of the number of cells initially infected in the absence or presence of 10 $\mu$M AZT. As can be seen in Table 1, the prevalence of colony formation after infection in the presence of AZT was similar (~5×10$^{-4}$) with the two preparations of HIV-gpt. This similarity is very distinct from the results of infections performed in the presence of a nonnucleoside reverse transcriptase inhibitor, TIBO R82150. In those studies, the prevalence of infection with the COS-cell derived virus was twenty fold lower than infection with HIV-gpt. rescued by replication-competent virus (26). Since the HIV-gpt produced in COS cells would not be expected to be genetically diverse, this relatively high rate of infection in the presence of AZT was not likely due to the detection of viral encoded-AZT resistance. Similarly, the absence of more prevalent infection in the presence of AZT when HIV-gpt was produced by rescue with a propagated stock of replication-competent HIV, implies that true genetic resistance was not being detected in these experiments. These data suggest that other mechanisms may contribute to this early viral breakthrough in the presence of AZT.

Figure 2:
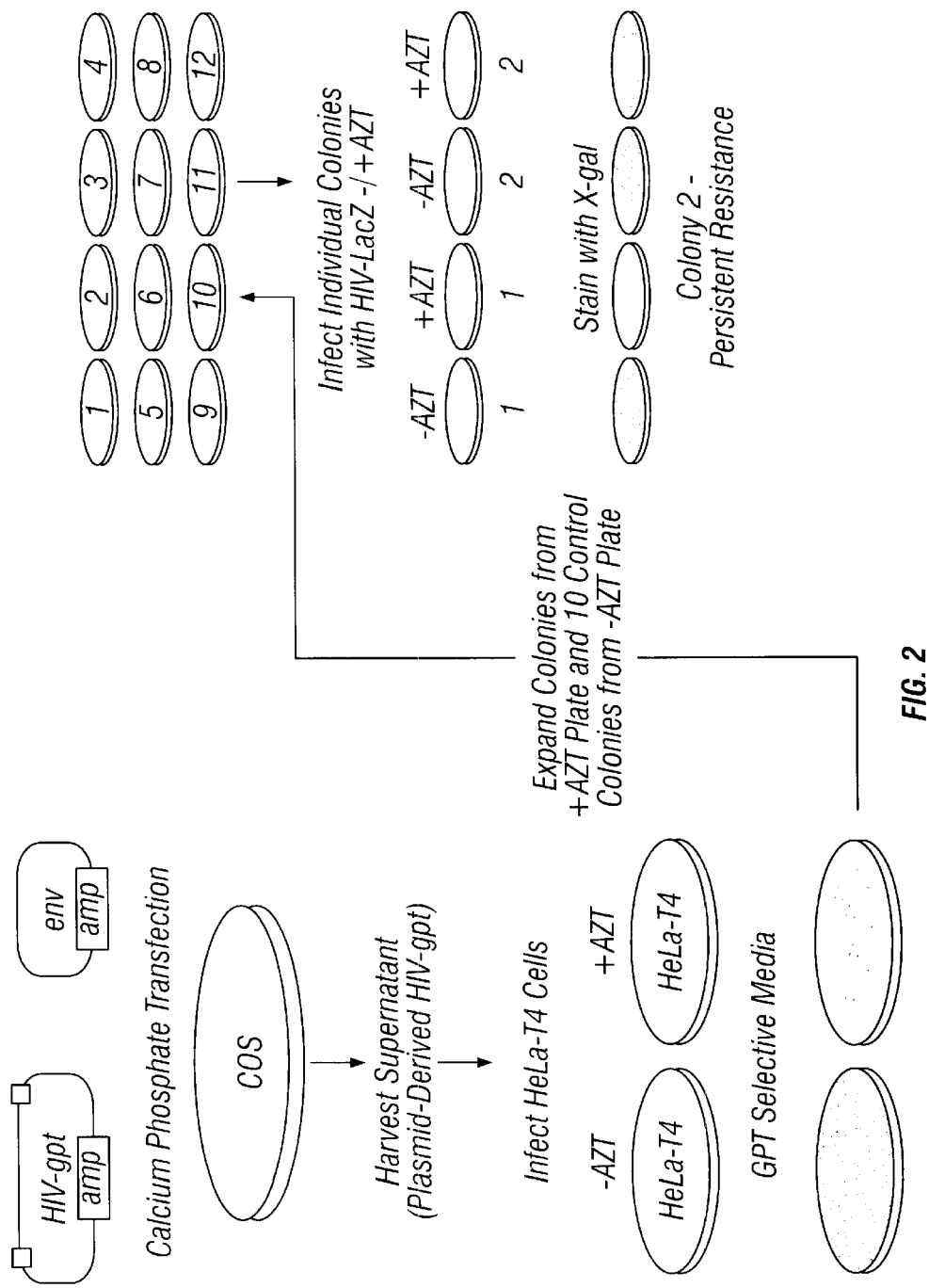
FIG. 2 is a schematic representation of the analysis of colonies arising after COS cell derived HIV-gpt infection of HeLa-T4 cells in the presence of 10 $\mu$M AZT.

Identification of Cells Refractory to the Antiviral Effects of Nucleoside Analogs To characterize further the mechanism(s) of viral infection accounting for the high frequency of colony formation after infection in the presence of 10 $\mu$M AZT, the experiment depicted in FIG. 2 was performed. HeLa-T4 cells were infected with HIV-gpt (prepared in COS cells) in the absence or presence of AZT. Infected cells were selected in gpt selective media and colonies were isolated and expanded into cell lines. Twelve cell lines developing after infection in the presence of AZT were further characterized. To determine if these cell lines were refractory to the antiretroviral effects of AZT they were infected with HIV-LacZ in the presence of 10 $\mu$M AZT. Three days after infection, the cells were stained with X-gal to detect 13-galactosidase activity. Nine of these twelve cell lines behaved like wild type HeLa-T4 cells with complete inhibition of infection in the presence of AZT. However, three of these cell lines demonstrated greater than 50% of control infection (−AZT) despite the presence of 10 $\mu$M AZT. These cell lines were labeled as "persistently resistant" to the antiretroviral effects of AZT.

Figure 3:
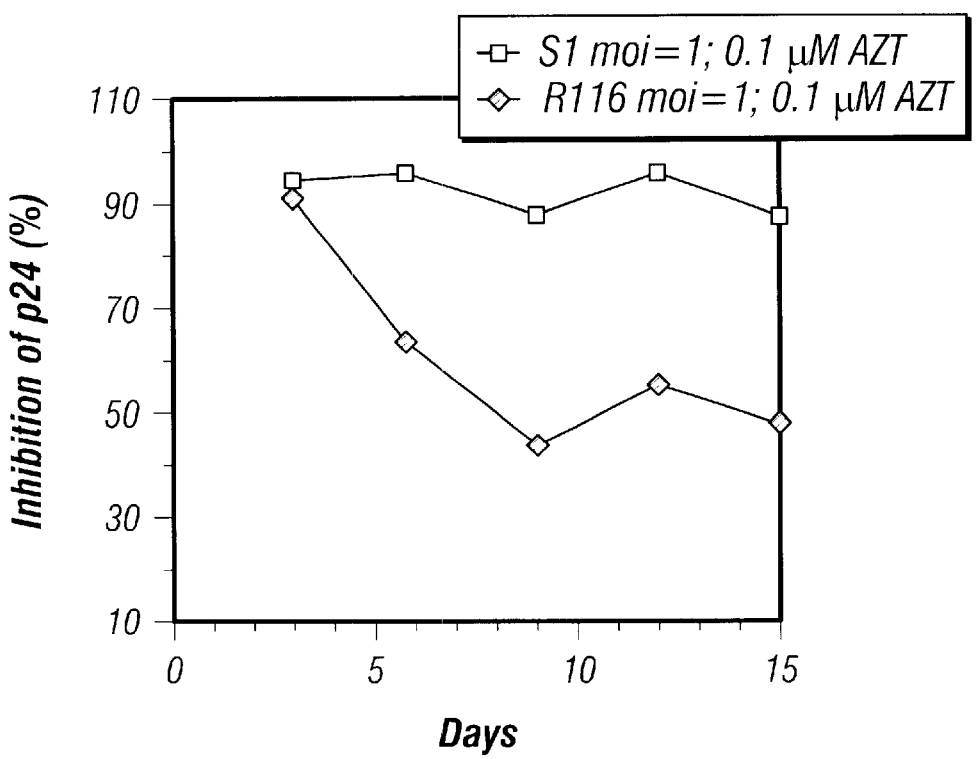
FIG. 3 is a graph showing the infection of a clone of HeLa-T4 cells "persistently resistant" to the antiviral effects of AZT (clone R116) and a control clone (S1) with replication-competent HIV-1IIIB in the presence of 0.1 $\mu$M AZT.

Infection of these "persistently resistant" cell lines with replication-competent HIV confirmed the relative inefficacy of AZT in these cells. For example, a clinically relevant concentration of 0.1 $\mu$M AZT was much less effective in inhibiting HIV-1IIIB in the "persistently resistant" cell line than in the control cells (FIG. 3). No such cells resistant to the antiviral effects of AZT were obtained when colonies derived from HIV-gpt infections in the absence of AZT were studied (see Table 2).

None of the "persistently resistant" cell lines were cross "resistant" to the antiretroviral effects of ddl or ddC. Interestingly, cells with persistent resistance to AZT showed partial cross resistance to the antiretroviral effects of 50 $\mu$M d4T. In addition to this evaluation for cellular cross-resistance, it was possible to use a similar experimental protocol to demonstrate the independent selection of cells refractory to the antiretroviral effects of a variety of other nucleoside analogs (Table 2). In contrast, no cells "persistently resistant" to the antiretroviral effects of the non-nucleoside reverse transcriptase inhibitor TIBO R82150 could be selected using identical techniques. These results indicate that HeLa-T4 cells have subpopulations of cells that are independently refractory to the antiretroviral effects of a variety of nucleoside analogs.

Comparison of Thymidine and AZT Phosphorylation in Isolated Clones

Figure 4A:
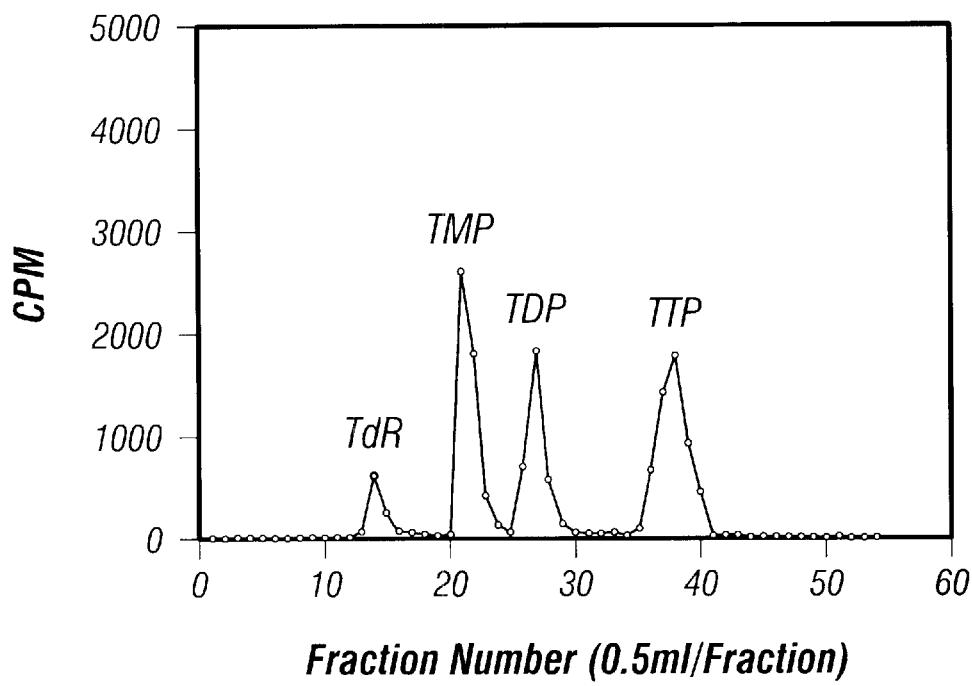
FIGS. 4A and 4B are graphs illustrating thymidine metabolism-HPLC analysis of clones obtained after infection of HeLa-T4 cells with HIV-gpt in the presence and absence of AZT.
Figure 4B:
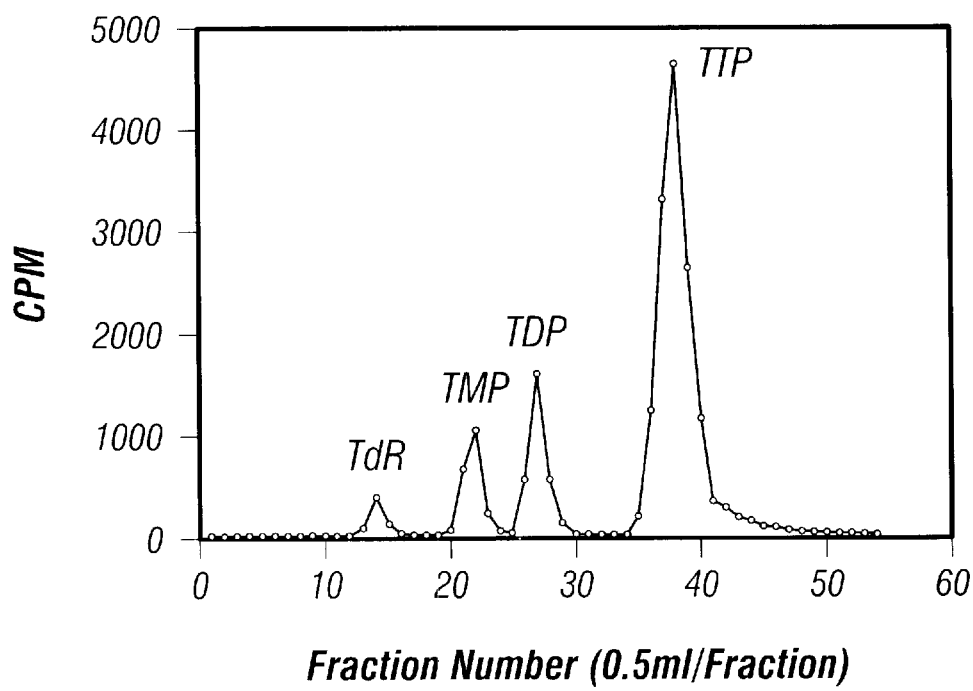
Figure 5A:
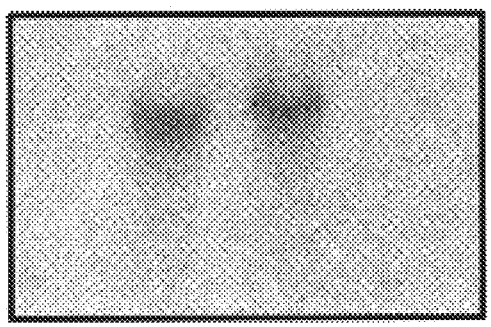
FIG. 5 is a graph showing a comparison of thymidine kinase mRNA levels (A) and enzyme activity (B) in cell lines sensitive and persistently resistant to the antiretroviral effects of AZT.
Figure 5B:
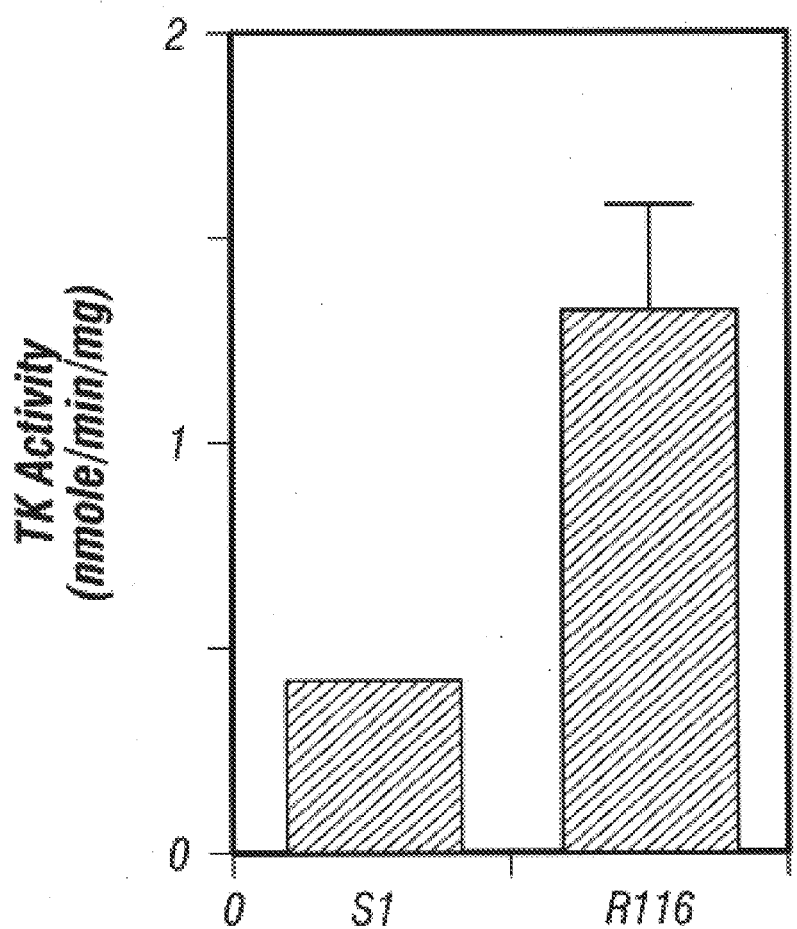

To initiate an analysis of the mechanisms responsible for this cellular resistance, a persistently resistant cell line was compared to a control cell line obtained by HIV-gpt infection in the absence of AZT. Each of these cell lines was incubated with $^3$H-thymidine and thymidine metabolites were assayed by HPLC. As shown in FIGS. 4A and 4B, the persistently resistant cell line (R116) had a greater phosphorylation of thymidine into TTP compared to the non-resistant cell line (S1). An identical experiment with $^3$H-AZT indicated a nearly 2 fold reduction in AZTTP in R116 cells compared to S1 cells (Table 3). Therefore, a component of the resistance may be related to a diminished AZTTP/TTP ratio. These results suggest that alterations in nucleotide metabolism may underlie some of the differences between these cell lines. To further characterize the basis for these differences, thymidine kinase mRNA levels and thymidine kinase activity were compared in the two cell lines. Although there were no differences in the thymidine kinase mRNA levels on a Northern blot analysis, the R116 cell line had 3 times greater thymidine kinase activity than the S1 cell line (FIG. 5).

Tolerance of the Clones to Very High Concentrations of AZT

Figure 6:
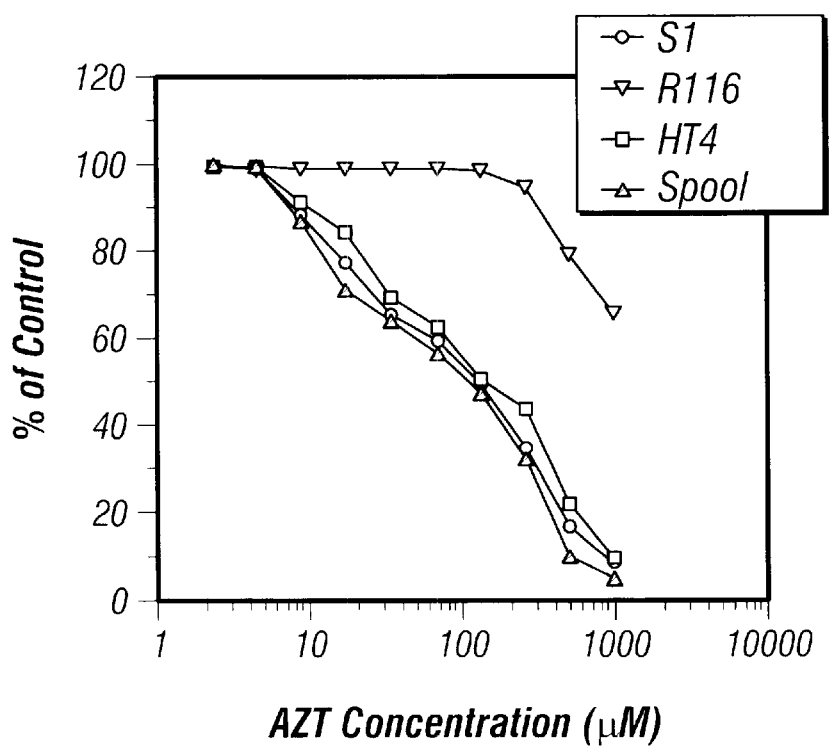
FIG. 6 is a graph showing cellular toxicity of AZT.

In additional studies of these cell lines, tolerance of high concentrations of AZT was tested. As shown in FIG. 6, the persistently resistant cell line (R116) was much more tolerant of high concentrations of AZT. The cytotoxic concentration of AZT that killed 50% of a variety of control cell lines was approximately 100 μmM. In contrast, the cytotoxic concentration of AZT that killed 50% of the persistently resistant clone R116 was greater than 1 mM. This implies that the mechanisms that protect HIV from AZT in the resistant cell lines also protect these cell lines from the cytotoxic effects of even higher concentrations of AZT. This demonstrates another AZT-related difference amongst these clones derived from the same parental cell line.

Use of Floxuridine to Modulate the Antiviral Activity of AZT

Figure 7A:
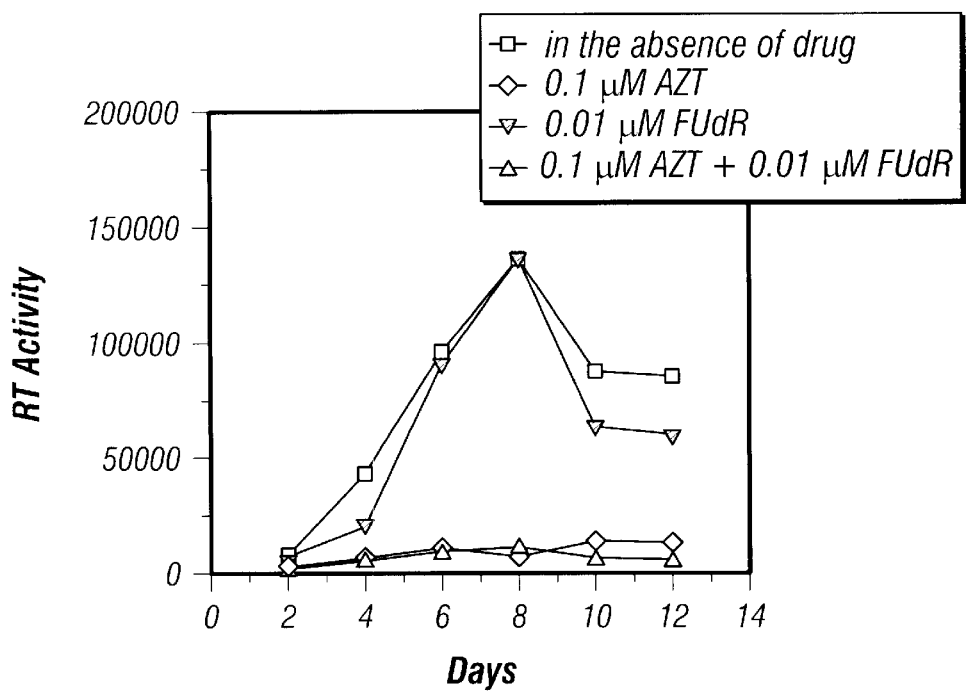
FIG. 7A and FIG. 7B are graphs showing the suppression of viral breakthrough in cells sensitive and refractory to the antiviral effects of AZT.
Figure 7B:
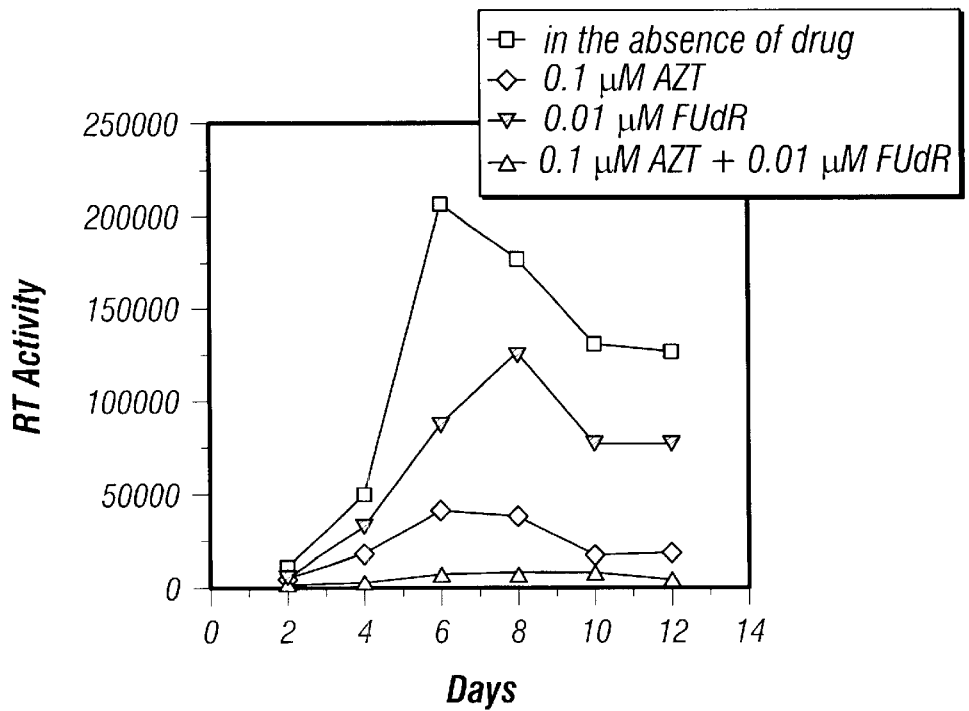

Inhibition of Early Viral Breakthrough in Cells Sensitive and Refractory to the Antiretroviral Effects of AZT A previous study has utilized replication-defective HIV to quantitate early infection in the presence of AZT (31). In that study, HIV-gpt (a recombinant HIV encoding a selectable marker) was used to infect HeLa-T4 cells in the presence of AZT. Infected cells were isolated in gpt selective media and expanded into cell lines. Several such cell lines were refractory to the antiviral effects of AZT as evidenced by the ability of replication-defective or replication-competent HIV to infect these cells in the presence of AZT. Several control cell lines were obtained by infection of HeLa-T4 cells with HIV-gpt in the absence of AZT. Cell line R116 is a cell line that was determined to be refractory to the antiviral effects of AZT. Cell line S1 is a control cell line. A prior metabolic analysis of these cell lines indicated that cell line R116 had a reduced accumulation of AZTTP and an increased phosphorylation of thymidine to TTP in comparison to the S1 control cell line (31). To determine if the addition of a fluoropyrimidine to AZT increased the antiviral efficacy of AZT in the R116 cell line, cells were cultured in the absence or presence of 0.1 μM AZT or 0.01 μM FUdR alone or in combination prior to infection with HIV-1IIIB at an input multiplicity of infection of 1. As demonstrated in FIG. 7A, 0.1 μM AZT had potent antiviral efficacy in the control S1 cell line. In contrast, in the cell line refractory to the antiviral effects of AZT (R116) there was significant HIV replication in the presence of 0.1 μM AZT (FIG. 7B). However, the addition of 0.01 μM FUdR to 0.1 μM AZT suppressed this viral breakthrough. At these concentrations, no cytotoxicity was observed.

Figure 8:
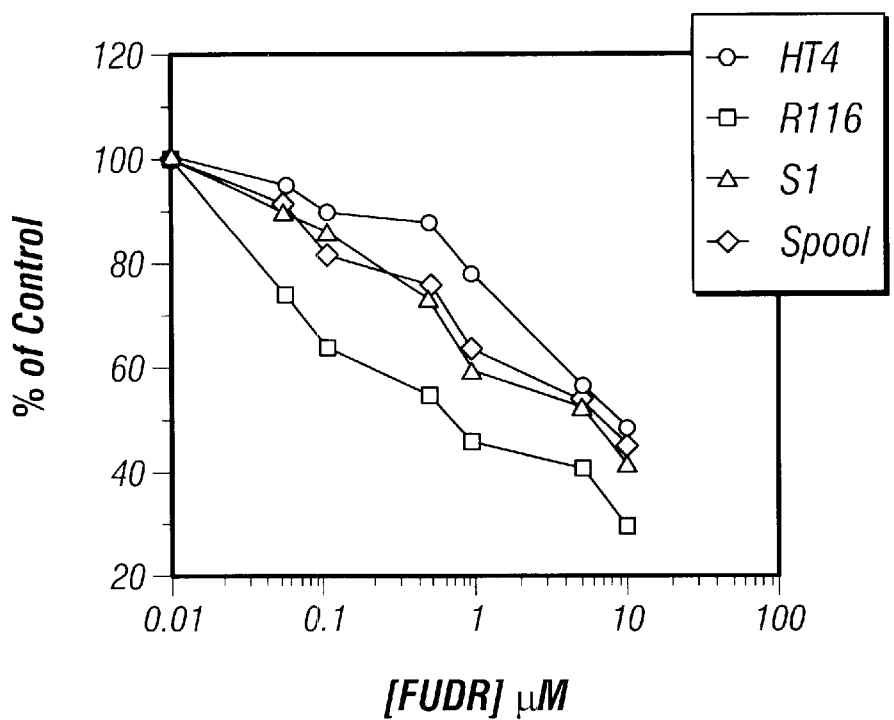
FIG. 8 is a graph illustrating FUdR cytotoxicity in cells sensitive and refractory to the antiretroviral activity of AZT.

To further characterize these different cell lines, cytotoxicity to various concentrations of FUdR were determined. As shown in FIG. 8, the R116 cell line had an $ED_{50}$ of 0.7 μM FUdR whereas the S1 cell line, parental HeLa-T4 cells and a pool of control cell lines all had an ED50 of 7 μM. These results further substantiate the presence of metabolic differences in cells refractory to the antiviral effects of AZT as opposed to cells sensitive to the antiviral effects of AZT.

Efficacy of AZT in Combination with FUdR in Inhibiting HIV-1 Infection of Lymphoid cells Sensitive and-Refractory to the Antiviral Activity of AZT To extend the analysis of the antiviral efficacy of AZT in combination with FUdR to lymphoid cells, similar experiments were performed in Jurkat JE6.1 cells. In these experiments, three populations of cells were studied. The parental JE6.1 cells were compared to populations of JE6.1 cells that were isolated after infection with a replication-defective recombinant Moloney Leukemia virus containing the Tn5 neo gene (MLV-neo) in the absence or presence of AZT. JE6.1 cells were infected in the absence or presence of 10 μM AZT and two days later the cells were placed in media containing 1 mg/ml G418 to allow the growth of infected cells. JE6.1AZTR is the cell population that was infected with MLV-neo in the presence of AZT. JE6.1con is the control population of cells infected with MLV-neo in the absence of AZT.

The efficacy of AZT in combination with FUdR in inhibiting HIV-1 infection of these cell populations was determined by infection in the absence of AZT or in the presence of 0.001 μM, 0.01 μM, 0.1 μM, 1 μM or 10 μM AZT in combination with no FUdR, 0.005 μM FUdR, 0.01 μM FUdR or 0.025 μM FUdR. This experiment allowed a detailed analysis of the $IC_{50}$ of AZT in each population with different concentrations of FUdR. These results are shown in Table 4. Based upon prior results in HeLa-T4 cells (31), it is likely that the JE6.1AZTR cells represent a mixture of cells, some of which require an increased concentration of AZT to inhibit HIV infection. This is reflected by a 2 fold increase AZT $IC_{50}$ when analyzing the entire population. Strikingly, the combination of FUdR with AZT dramatically suppresses HIV infection of this population. A greater than 600 fold reduction of AZT $IC_{50}$ is seen during infection of these cells in the presence of AZT and FUdR. In fact, these cells, which were initially isolated as cells infected in the presence of AZT, were more sensitive to the antiviral effects of the AZT-FUdR combination than were control or parental cells. These results suggest that this population of cells has metabolic features that renders them highly susceptable to the antiviral effects of the AZT-FUdR combination. Of note, there is a 10-fold reduction of AZT $IC_{50}$ when the parental and control cell populations were infected with HIV-1 in the presence of AZT and FUdR. No cytotoxicity was observed in the AZT-FUdR combination except at the highest drug concentrations used (10 μM AZT plus 0.025 μM FUdR, FIG. 9).

Figure 10A:
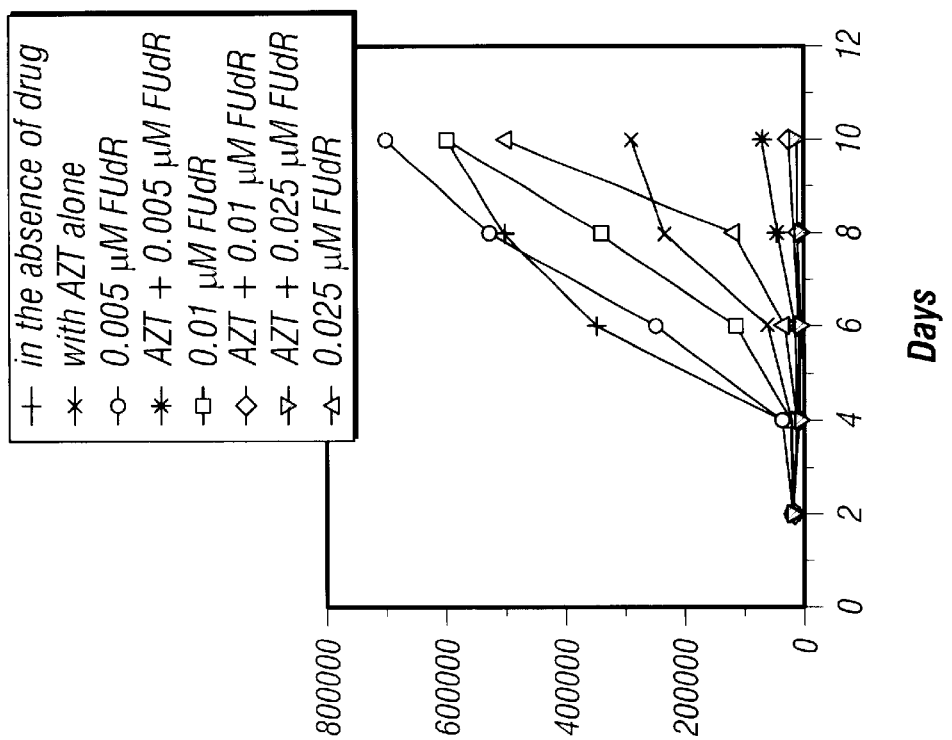
FIG. 10 and FIG. 10B are graph's showing that the AZT-FUdR combination inhibits HIV-1 infection of PBMC.
Figure 10B:
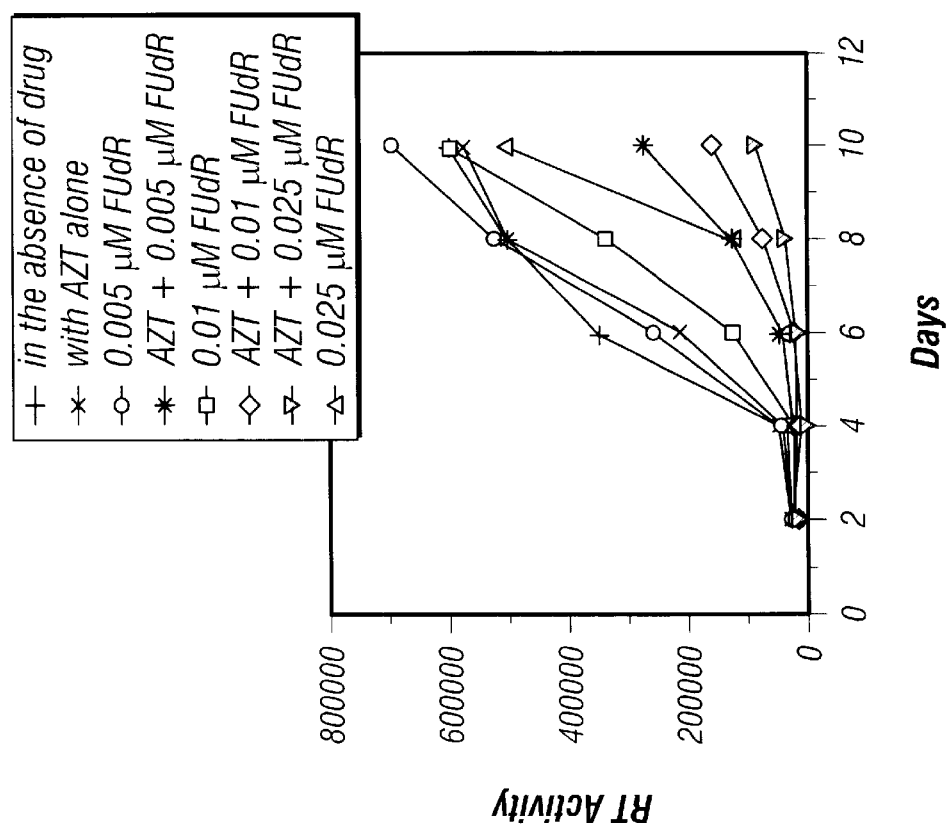

Efficacy of AZT in Combination with FUdR in Inhibiting HIV-1 Infection of Primary Blood Mononuclear Cells The antiviral efficacy of the combination AZT and FUdR was also assessed in PBMC. These studies are shown in FIG. 10 and demonstrate that the combination of AZT and FUdR has potent antiviral activity in PBMC. Similar results were obtained with a primary HIV isolate known to be genetically sensitive to AZT. Therefore, FUdR potentiates the antiviral efficacy of AZT in PBMC infected with either HIVIIIB or a clinical isolate. Of note, cytotoxicity in the AZT-FUdR combination was similar to that seen for the JE6.1 cells in that cytotoxicity was only observed when 10 μM AZT was combined with 0.025 μM FUdR.

Early HIV Breakthrough Infection in the Presence of Stavudine

Preliminary Characterization of Mechanisms Allowing HIV Infection in the Presence of d4T To undertake a preliminary characterization of the predominant mechanisms responsible for early HIV infection after the initiation of d4T, we utilized several populations of recombinant viruses. Recombinant replication-defective HIV was prepared by transfection of COS cells with complementing plasmids encoding the RNA and proteins necessary for the production of a recombinant HIV encoding gpt (26). Such viruses are produced without major genetic heterogeneity as the predominant mechanisms responsible for the generation of heterogeneity (e.g., cycles of reverse transcription) are not involved in the production of these viruses. Even if there was heterogeneity as a consequence of errors during plasmid transcription, the resulting mutated proteins would be greatly diluted in a population of proteins. In contrast, replication defective HIV-gpt made by rescue with replication-competent HIV will contain proteins encoded by the replication-competent virus used for rescue. Prior experiments have demonstrated the close relationship between the drug sensitivity phenotype of the recombinant virus and the drug sensitivity phenotype of the virus used to rescue the recombinant virus (26). Therefore, recombinant virus produced by rescue with replication-competent virus will be heterogeneous and may reflect the drug sensitivity profile of the virus used for rescue. In a prior experiment, the heterogeneity introduced by the replication-competent virus used for rescue resulted in a calculation of the prevalence of HIV resistant to a NNRTI in an unselected population (26). This calculated value was very similar to the prevalence subsequently calculated from in vivo studies of HIV dynamics after the initiation of a NNRTI (38).

A comparison of the two virus populations described above demonstrated very similar rates of infection in the presence of high concentrations of d4T (Table 5). This high level of infection with a virus produced from plasmid transcripts (HIV-gpt) suggested a high rate of infection with a homogenous population of a recombinant virus whose proteins were generated by translation of plasmid transcripts and thus not anticipated to have a high level of genetic heterogeneity. To confirm this high rate of infection in the absence of genetic drug resistance, we used several other recombinant viruses and host cells. MLV based recombinant viruses showed a similar high rate of infection in the presence of d4T (Table 6). Similar infections in the presence of high concentrations of other nucleoside reverse transcriptase inhibitors have consistently demonstrated a rate of infection in the presence of high concentrations of d4T greater than that seen in the presence of high concentrations of the other nucleoside analogs (Table 6). A high rate of infection of Jurkat cells in the presence of d4T has also been seen.

The similar rates of infection with virus prepared by plasmid transfection and virus prepared by rescue with replication-competent HIV suggested that genetic resistance was not the major mechanism of early HIV breakthrough being detected. This interpretation was supported by evidence of high rates of infection with MLV based recombinant virions (also anticipated to have a low level of genetic heterogeneity). Infections of Jurkat cells indicated that the high rate of infection in the presence of high concentrations of d4T was not cell line specific. These data suggested that early HIV breakthrough infection in the presence of d4T was not due to infection by d4T-resistant virus.

Isolation of the Cells Infected With HIV in the Presence of d4T

Figure 11:
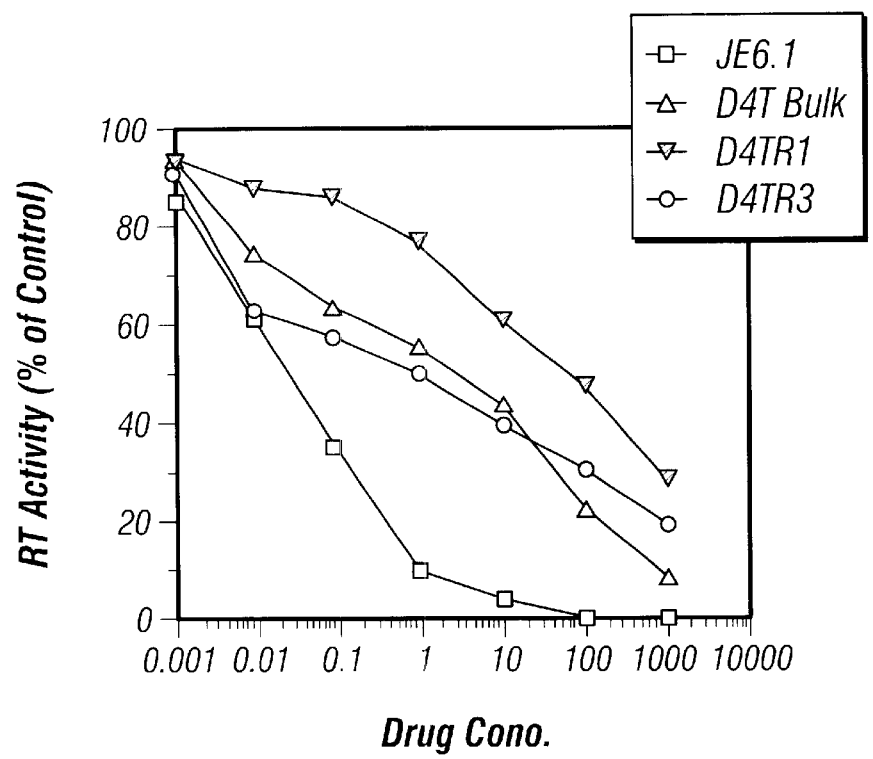
FIG. 11 is a graph showing the infection of JE6.1 cell clones persistently resistant to the antiviral effects of d4T (D4T bulk, D4TR1, D4TR3) and a control clone of JE6.1 cells with HIV-IIIB in the presence of various concentrations of d4T.

The presence of a selectable marker gene in the recombinant HIV allowed the isolation of cells infected by the recombinant viruses in the presence of d4T. These cells were characterized by infection with both additional recombinant viruses and by replication-competent viruses. As demonstrated in Table 6, approximately 37% of the isolated cells were repeatedly refractory to the antiviral effects of d4T (i.e., they could be readily re-infected with recombinant HIV, recombinant MLV, or replication-competent HIV in the presence of high concentrations of d4T). An even higher percentage of the Jurkat cells infected in the presence of d4T were persistently refractory to the antiviral effects of d4T (Table 7). Infections with replication-competent HIV demonstrated that the refractoriness to infection detected in these clones was not a phenomena solely associated with recombinant viruses (FIG. 11). A subset of these persistently refractory cells (approximately 20%) were also refractory to the antiviral effects of AZT.

Combined d4T-FUdR Antiviral Activity

Figure 12:
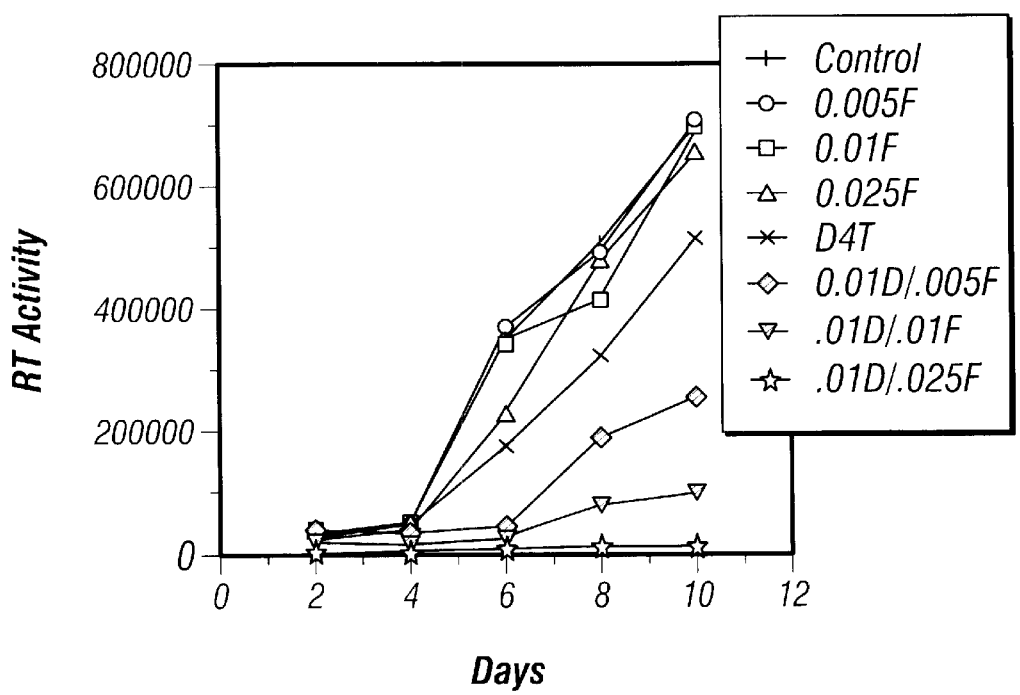
FIG. 12 is a graph showing that the D4T-FUdr combination inhibits HIV-1 infection of PBMCs.

As has been demonstrated previously for AZT, a component of the refractoriness to the antiviral effects of d4T can be reversed by the addition of FUdR (Table 8). The antiviral efficacy of the combination therapy, as measured by the d4T IC50, is markedly improved with combination therapy. Prior studies of the antiviral efficacy of FUdR have demonstrated limited antiviral efficacy of FUdR alone, but marked antiviral efficacy of combined AZT and FUdR. Table 8 shows the capacity of the FUdR-d4T combination to reverse some of the cellular refractoriness to d4T described above. The FUdR-d4T combination has marked antiviral activity in cells demonstrated to be refractory to the antiviral effects of d4T. The antiviral efficacy of the combination has also been studied in unselected PBMC (FIG. 12).

Discussion

Sanctuary Growth of HIV in the Presence of AZT

The studies described above indicate that sanctuary growth of HIV may occur in the presence of AZT and that early in treatment cellular resistance may make a large contribution to viral breakthrough. In fact, there was no quantitative difference in HIV breakthrough when HIV-gpt prepared by transfection in COS cells was compared to HIV-gpt produced by rescue with replication-competent HIV. This suggests that a large part of early infection in the presence of AZT may be a consequence of cellular effects. At least two types of such sanctuary growth were detected. Nine of the twelve cell lines analyzed did not have persistent resistance to the antiviral effects of AZT and may have had epigenetic alterations such as those that might occur at specific points in the cell cycle. In contrast, three of the twelve cell lines had persistent resistance to the antiviral effects of AZT, with both recombinant and replication-competent HIV. In studies with replication-competent HIV, virtually complete inhibition of the infection of control cells was obtained with a concentration of AZT that only reduced viral production in a persistently resistant clone by 50%.

These cell lines refractory to the antiviral effects of AZT are likely to have specific alterations that render AZT less effective. Metabolic studies suggest that some of this resistance may be due to differences in nucleotide metabolism resulting in a reduction of AZTTP in the resistant cells. It will be important to further characterize and define the mechanisms responsible for cellular resistance because reversal of this resistance may greatly reduce viral burden and delay the outgrowth of virus with genetic resistance. It is important to emphasize that the cells that were detected as refractory to the antiviral effects of AZT were only exposed to AZT for a short period of time. There was no preselection of cells prior to infection with the recombinant viruses.

Recent reports on nucleotide pool sizes in resting as opposed to stimulated blood mononuclear cells and different cell lines derived from different blood cell lineages have demonstrated marked differences that might translate into variable efficacies of nucleoside analogs within populations of blood cells (6,15). Furthermore, other investigators have grown cells in high concentrations of AZT for prolonged periods of time and demonstrated the selection of cells with reduced levels of thymidine kinase activity (17). Additional data about metabolic differences occuring in the lymphocytes of patients treated with prolonged courses of AZT also suggests that cellular resistance may contribute to HIV breakthrough (1). Thus, cellular resistance is likely to contribute to viral breakthrough during an in vivo infection and multiple mechanisms may contribute to cellular resistance. The prevalence of resistant cells detected in single cell lines derived during infection in these studies raises interesting speculation concerning the prevalence of similar resistant cells during an in vivo infection involving multiple cell types.

Earlier studies with recombinant viruses indicated that there is a high prevalence of genetically TIBO resistant HIV in an unselected HIV population. As a consequence of this high prevalence and the lack of cellular metabolism for TIBO, genetically resistant virus is rapidly selected in vivo and in vitro. In contrast, AZT is metabolized in cells, a subpopulation of which is refractory to the antiretroviral effects of AZT. Early growth of "non-genetically resistant" virus can occur in these sanctuary cells ("cellular resistance"). With continued growth there is amplification of pre-existing (or emerging) viral variants with genetic resistance because the truly resistant virus can infect any suitable target cell, not just those cells in which AZT is ineffective. This gives a relative growth advantage to the genetically resistant virus. Subsequent additional mutations or recombination events may result in viruses with multiple mutations. The initial "cellular resistance" may allow a population of non-resistant or partially resistant virus to replicate, providing a pool of virus in which additional mutations and recombination events can occur. Reversal of cellular resistance could conceivably delay, or even prevent, the outgrowth of highly resistant virus with multiple mutations by not allowing non-resistant or partially resistant virus (with single mutations) to replicate.

FIG. 1 is a schematic representation of the production of recombinant HIV-gpt by COS cell transfection or rescue from the H9/HIV-gpt cell line.

FIG. 2 is a schematic representation of the analysis of colonies arising after COS cell derived HIV-gpt infection of HeLa-T4 cells in the presence of 10 $\mu$M AZT. Twelve such colonies were expanded and infected with HIV-LacZ in the presence and absence of 10 $\mu$M AZT. Ten control colonies derived from HIVgpt infection of HeLa-T4 cells in the absence of AZT were studied in parallel. "Persistent" cellular resistance was defined by a high level infection with HIVLacZ in the presence of AZT, as shown for colony number 2. HIV-LacZ contains the LacZ gene driven by an SV40 promoter inserted into a large deletion in the HIV genome extending from the pol gene to the 3' end of the env gene. HIVLacZ virus production has been previously described (16).

FIG. 3 is a graph showing the infection of a clone of HeLa-T4 cells "persistently resistant" to the antiviral effects of AZT (clone R116) and a control clone (S1) with replicationcompetent HIV-1IIIB in the presence of 0.1 $\mu$M AZT. P24 was assayed, compared to a control infection in the absence of AZT and plotted as a function of time. P24 values in the absence of AZT were 1857+104 ng/ml for S1 and 1717+113 ng/ml for R116.

FIGS. 4A and 4B are graphs illustrating thymidine metabolism-HPLC analysis of clones obtained after infection of HeLa-T4 cells with HIV-gpt in the presence and absence of AZT. FIG. 4A illustrates the S1 cell line derived from HeLa-T4 cells after infection with HIV-gpt in the absence of AZT. FIG. 4B illustrates the R116 cell line, which was persistently resistant to the antiviral effects of AZT. The earliest peak represents thymidine and the subsequent peaks represent TMP, TDP, and TTP.

FIG. 5 is a graph showing a comparison of thymidine kinase mRNA levels (A) and enzyme activity (B) in cell lines sensitive and persistently resistant to the antiretroviral effects of AZT. The mRNA levels of S1 and R116 were 8390 and 8500 densitometry units, respectively. Thymidine kinase activity was based upon three independant experiments performed in triplicate.

FIG. 6 is a graph showing cellular toxicity of AZT. The cell lines were grown in the presence of the indicated concentrations of AZT. Cellular toxicity was then determined in cells persistently refractory to the antiviral effects of AZT (R116) and in cells sensitive to the antiviral effects of AZT (HT4, S pool and S1) using a standard MTT assay. S pool was a pool of colonies derived from HIV-gpt infection of HeLa-T4 cells in the absence of AZT. HeLa-T4 is the parental cell line.

Table 1 shows the frequency of HIV-gpt colony formation in the presence and absence of AZT. Table 1 also shows a comparison of HIV-gpt produced in COS cells by transfection with plasmids and HIV-gpt produced by rescue from the H9/HIV-gpt cell line after infection with HIV-1lilB (see FIG. 1).

TABLE 1

| | Number of colonies | | |
|---|---|---|---|
| Source of HIV-gpt | −AZT | +AZT | Frequency |
| Plasmid-derived (COS cells) | 3.1 × 10$^4$ | 16 | 5.2 × 10$^{-4}$ |
| Rescue with HIV-1 | 1.8 × 10$^4$ | 9 | 5.0 × 10$^{-4}$ |

Table 2 shows colony formation and "persistent resistance" after HeLa-T4 infection with plasmid derived HIV-gpt (produced in COS cells) in the presence of high doses of the indicated antiretroviral agents. Concentrations of the antiretroviral agents were: AZT-10 $\mu$M, DDI-50 $\mu$M, D4T-50 $\mu$M and DDC-10 $\mu$M.

TABLE 2

| Drug | Number of colonies | Number of "persistently resistance" colonies | Frequency |
|---|---|---|---|
| No Drug (Control) | 8800 | 0/10 | 0 |
| AZT | 12 | 3/12 | 3.4 × 10$^{-4}$ |
| D4T | 50 | not done | — |
| DDI | 16 | 2/16 | 2.3 × 10$^{-4}$ |
| TIBO | 3 | 0/3 | 0 |

Table 3 shows the concentration of phosphorylated AZT metabolites in the "persistently resistant" (R116) and sensitive (S1) cell lines. Pool sizes were determined by incubation of cells with $^3$H-AZT for 4 hours followed by cellular extraction and HPLC. The numbers are expressed as pmoles/10$^6$ cells. The numbers in parentheses represent the percentage of total radioactive species in that pool.

TABLE 3

| Clone | AZT | AZTMP | AZTDP | AZTTP |
|---|---|---|---|---|
| S1 | 0.0206 (12.2) | 0.1212 (71.6) | 0.0116 (6.9) | 0.0158 (9.3) |
| R116 | 0.0155 (7.7) | 0.1575 (78.6) | 0.0193 (9.6) | 0.0083 (4.2) |

Use of Floxuridine To Modulate the Antiviral Activity of AZT

Preliminary studies from our laboratory have demonstrated that early HIV infection of various cell lines in the presence of AZT is not the consequence of infection with AZT-resistant virus. In both HeLa-T4 cells and a lymphoid cell line (Jurkat JE6.1), the predominant component of early HIV infection in the presence of AZT is a consequence of infection with AZT-sensitive virus (31). Clinical studies also demonstrate that early HIV infection in the presence of AZT occurs with AZT-sensitive virus (29). To characterize the mechanisms allowing the replication of AZT-sensitive HIV in the presence of AZT, a metabolic analysis of some of the cells infected with HIV in the presence of AZT in vitro was previously undertaken (31). Those studies demonstrated that a component of early infection with drug-sensitive virus was occuring in a subpopulation of cells with features that would be anticipated to decrease the antiviral efficacy of AZT. These studies were important because they indicated that the reversal of early HIV infection in the presence of AZT required interventions directed at features other than viral drug-resistance. Based upon a prior study demonstrating increased phosphorylation of thymidine to TTP and decreased AZTTP in a subset of cells infected with drug-sensitive HIV in the presence of AZT, applicants have attempted to modulate the antiviral efficacy of AZT by combining AZT therapy with floxuridine. These initial studies have demonstrated the suppression of early viral breakthrough infection in the presence of AZT with drug combinations that are readily achievable in vivo and are non-cytotoxic. In addition, there is a clear concentration-response relationship when FUdR is added to AZT.

In addition to the determination that the AZT-FUdR combination suppressed HIV infection of cells that were infected with HIV in the presence of AZT, the combination was much more effective than AZT alone at inhibiting HIV infection of an unfractionated lymphoid cell line and PBMC. This in creased efficacy was also demonstrated wit h a clinical isolate. Therefore, the enhanced antiviral activity of the combination therapy is not restricted to cell lines, recombinant viruses, or laboratory strain s of virus and may therefore have clinical utility.

The increased efficacy of AZT-FUdR in suppressing HIV infection of cells readily infected with HIV in the presence of AZT is particularly striking. Since this population of cells is a mixture of cells with and without persistent refractoriness to the antiviral effects of AZT (i.e., infection of a subset of this population is repeatedly refractory to the antiviral effects of AZT), the AZT $IC_{50}$ for this population is only minimally elevated. Nevertheless, infection of this entire population is extremely sensitive to inhibition by the AZT-FUdR combination. The supersensitivity of infection of this population of cells to combination therapy was unanticipated and is likely to be explained by metabolic features that are responsible for the efficacy of the combination. Determination of the mechanisms responsible for this supersensitivity to combined AZT-FUdR therapy must await metabolic analysis of thymidine, AZT and FUdR phosphorylated intermediates in populations of cells and individual clones. It is important to note that in all of these studies FUdR has moderate antiviral activity when used by itself. The mechanisms by which this inhibition occurs are also currently unknown and may also be related to perturbations of normal thymidine metabolite pools, direct inhibition of viral or cellular processes or by incorporation into the viral DNA during reverse transcription.

It is very likely that the long term ability of HIV to replicate in the presence of AZT is a consequence of the emergence of AZT-resistant virus. Multiple mutations in RT are necessary for the development of this genetic AZT-resistance and these mutations emerge over several months-years. Suppression of early HIV replication with AZT sensitive virus in the presence of AZT could delay, or even prevent the emergence of AZT resistant virus by diminishing the substrate for subsequent genetic changes. Therefore, studies that define the mechanisms of early viral break through infection have potential long term therapeutic implications.

The clinical feasibility of combined fluoropyrimidine-AZT therapy needs to be evaluated. At low concentrations the fluoropyrimidines are often well tolerated by oncology patients with few significant neurologic, gastrointestinal or hematologic toxicities. The in vivo dose necessary to improve the antiviral efficacy of AZT will need to be determined, however extrapolation from in vitro studies indicates that cytotoxic concentrations of fluoropyrimidines will not be needed. Phase I clinical studies of FUdR combined with AZT in patients with HIV-1 infection will provide information about the feasability of combination therapy. In addition, other drugs with the ability to decrease TTP levels will also be evaluated in pre-clinical studies.

FIG. 7 is a graph showing the suppression of viral breakthrough in cells sensitive and refractory to the antiviral effects of AZT. Cells sensitive (S1) and refractory (R116) to the antiretroviral effects of AZT were infected with HIV-1 IIIB in the absence of drug (open squares), 0.1 μM AZT (solid squares), 0.1 μM FUdR (solid triangle) or a combination of 0.1 μM AZT plus 0.01 μM FudR (open triangle). Cell free supernatants were assayed for RT activity every two days. Results are the mean of triplicate cultures. Standard deviations were <15%.

FIG. 8 is a graph illustrating FUdR cytotoxicity in cells sensitive and refractory to the antiretroviral activity of AZT. Cells sensitive, parental HT4 (open circle), S1 (solid square), Spool (solid circle) and refractory, R116 (open square) were grown in the presence of various concentrations of FUdR. Three days latter, cell viability was determined by the MTT reduction method. Spool cells are a population of control cells obtained by infection with HIV-gpt in the absence of AZT (7).

Figure 9:
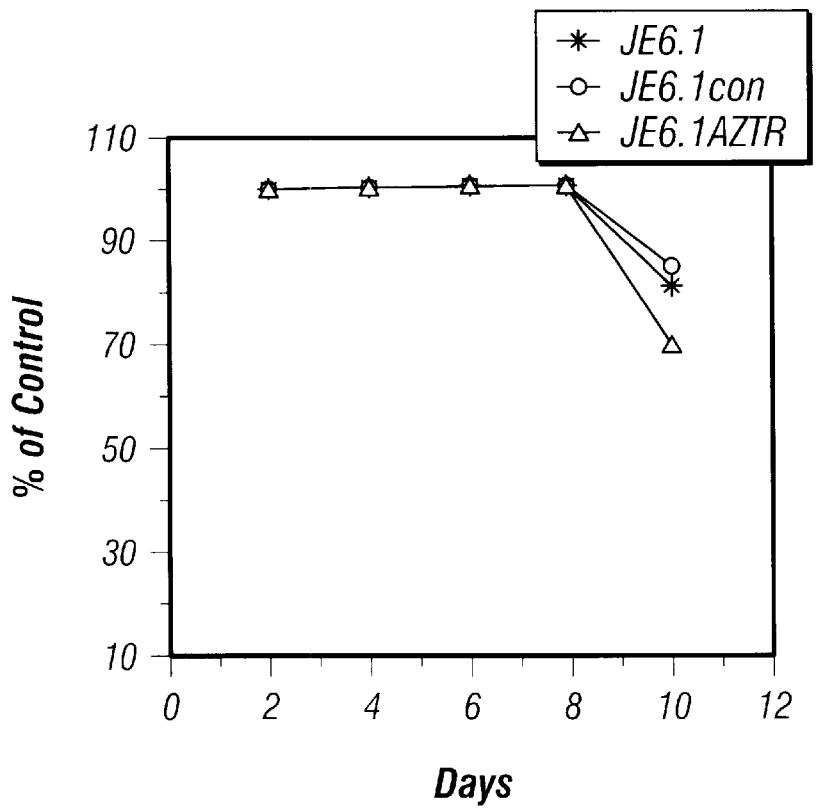
FIG. 9 is a graph showing AZT-FUdR cytotoxicity in JE6.1 cells sensitive and resistant to the antiviral effects of AZT.

FIG. 9 is a graph showing AZT-FUdR cytotoxicity in JE6.1 cells sensitive and resistant to the antiviral effects of AZT. Cytotoxicity of 10 μM AZT in combination with 0.025 μM FUdR was determined in JE6.1 cells sensitive (solid circle), JE6.1con (open circle) and resistant, JE6,1AZTR (open triangle) to the antiviral effects of AZT as described in Materials and Methods.

FIG. 10 is a graph showing that the AZT-FUdR combination inhibits HIV-1 infection of PBMC. PBMC were infected with HIV-1 in the absence of drug (cross) with AZT alone (x), with various concentrations of FUdR alone, [0.005 μM FUdR (open circle), 0.01 μM FUdR (open square), 0.025 μM FUdR (open triangle)], or with combinations of FUdR and AZT [AZT+0.005 μM FUdR (closed circle), AZT+0.01 μM FUdR (solid square) AZT+0.025 μM FUdR (solid triangle). Panel A, [AZT]=0.001 μM; Panel B, [AZT]=0.01 μM.

Table 4. Jurkat JE6.1 cells, Jurkat JE6.1 cells refractory to the antiviral effects of AZT (JE6. AZTR) and control JE6.1 cells (JE6.1con) obtained by infection with MLV-neo in the absence of AZT were infected with HIV-1 IIIB in the presence of 0.001 μM AZT, 0.01 μM AZT, 0.1 μM AZT, 1 μM AZT or 10 μM AZT in the presence of 0.005 μM FUdR, 0.01 μM FUdR or 0.025 μM FUdR. $IC_{50}$ represents the concentration of AZT required for 50% inhibition of reverse transcriptase activity at day 6 of infection.

TABLE 4

AZT/FUdR Susceptibility In Cells
Sensitive And Refractory To The Antiretroviral Activity Of AZT

|  | JE6.1 $IC_{50}$ Sensitivity | | JE6.1$_{AZTR}$ $IC_{50}$ Sensitivity | | JE6.1$_{Con}$ $IC_{50}$ Sensitivity | |
| --- | --- | --- | --- | --- | --- | --- |
| Treatment | (μM) | (fold) | (μM) | (fold) | (μM) | (fold) |
| AZT | 0.3 |  | 0.6 |  | 0.2 |  |
| AZT + .005F | 0.3 | 0 | 0.003 | 20 | 0.2 | 0 |
| AZT + .01F | 0.1 | 3 | 0.001 | 600 | 0.03 | 7 |
| AZT + .025F | 0.03 | 10 | <.001 | >600 | 0.02 | 10 |

Early HIV Breakthrough Infection in the Presence of Stavudine

Recent clinical analyses have emphasized the potential of prolonged suppression of HIV viremia when antiviral drug combinations are used (39,42). However, eradication of virus has not yet been demonstrated and virus regrowth with cessation of antiviral drugs is likely. In addition, the propensity of HIV with resistance to triple drug combinations (e.g., AZT, 3TC and a protease inhibitor) to emerge is still unclear. In the face of this uncertainty more detailed information concerning the mechanisms contributing to HIV breakthrough in the presence of antiviral drugs is needed.

In this report we utilize an in vitro model of HIV infection to provide two lines of evidence that early HIV breakthrough infection in the presence of d4T is not a consequence of infection by HIV with genetic drug resistance. Initial studies demonstrated that the frequency of HIV infection in the presence of d4T was very similar with several stocks of virus predicted to have significant differences in genetic heterogeneity. These studies suggested that any pre-existing unselected d4T resistant HIV in the population of HIV used to rescue the replication-defective HIV was not detected above the very high level of infection occurring with the other virus populations. The fact that nearly 50% of the cells infected with HIV in the presence of d4T are readily re-infected in the presence of high concentrations of d4T provides additional evidence supporting a high level of infection in the absence of genetic d4T resistance. These results are not limited to recombinant HIV and were also demonstrated with MLV based viruses as well as replication-competent HIV.

A subset of the cells infected with HIV in the presence of d4T do not have a persistent phenotype of being refractory to d4T. They may have been infected as a consequence of cell cycle related phenomena, intravirion reverse transcription (40) or other features that are not characterized by persistent cellular phenotypic change. The mechanisms underlying the refractoriness of both of the populations of cells (those with and those without persistent refractoriness to the antiviral effects of d4T) are currently being assessed with metabolic analyses.

Previous studies have demonstrated that the combination of FUdR with AZT or d4T has significant antiretroviral activity (41). Furthermore, the combination of FUdR and AZT has potent antiretroviral activity in cells refractory to the antiretroviral activity of AZT alone (31). These studies demonstrate the capacity to improve the antiviral efficacy of d4T by the addition of drugs such as FUdR with the capacity of interacting with the biochemical mechanisms responsible for AZT and/or d4T metabolic activation.

Several investigators have noted clinical features which are consistent with the results presented above. For example, the definition of genetic changes associated with clinical d4T resistance has been more difficult than the definition of genetic changes associated with AZT resistance. In addition, the selection of d4T resistant HIV in tissue culture has also more difficult than the selection of AZT resistant virus. The high level of early infection with drug sensitive virus might contribute to these features.

In summary, we have demonstrated that early HIV breakthrough infection in the presence of d4T is not a consequence of infection with virus that is resistant to d4T. As with AZT, infection with drug-sensitive virus predominates early after the initiation of the drug. Further analyses of the mechanisms responsible for HIV breakthrough in the presence of antiviral drugs are essential to efforts to define drug combinations that provide durable suppression of HIV infection and viremia (42). Clinical studies with FUdr may be warranted for selected patients intolerant of or not optimally responsive to current combination antiretroviral regimens containing either d4T or AZT.

FIG. 11 is a graph illustrating the infection of JE6.1 cell clones persistently resistant to the antiviral effects of d4T (D4T bulk, D4TR1, D4TR3) and a control clone of JE6.1 cells with HIV-IIIB in the presence of various concentrations of d4T. RT activity was assayed and compared with those for a control infection in the absence of d4T.

FIG. 12 is a graph showing that D4T-FUdr combination inhibits HIV-1 infection of PBMCs. PBMCs were infected with HIV-1 in the absence of drug [cross], with d4T alone (0.01 uM) [X], with various concentrations of FUdr alone (0.005 uM FUdr [open circle], 0.01 uM FUdr [open square], 0.025 uM FUdr [open triangle]) or with combinations of FUdr and d4T (d4T+0.005 uM FUdr [solid circle], d4T+0.01 uM FUdr [solid square], d4T+0.025 uM FUdr [solid triangle]).

Table 5. HIV-gpt produced in COS cells by transfection with plasmids (plasmid derived) is compared with HIV-gpt produced by, rescue from H9/HIV-gpt cell line after infection with HIV-IIIB and cells infected with MLV-neo.

TABLE 5

Frequency of HIV-gpt and MLV-neo Colony Formation in the Presence and Absence of D4T

| Sources of Virus | No. of colonies without D4T | No. of colonies with D4T | Frequency |
|---|---|---|---|
| plasmid derived | $4.7 \times 10^4$ | 80 | $1.7 \times 10^3$ |
| Rescue with HIV | $3.4 \times 10^4$ | 53 | $1.6 \times 10^3$ |
| MLV-neo | $9.2 \times 10^4$ | 101 | $1.1 \times 10^3$ |

Table 6. Colony formation and persistent resistance after Hela-T4 cell infection with MLV-neo virus in the presence and absence of various antiviral agents.

TABLE 6

Colony Formation and Persistent Resistance After Hela-T4 Infection With MEV-neo Virus in the Presence and Absence of Various Antiretroviral Agents*

| Drug | No. of colonies | No. of persistently resistant colonies | Frequency |
|---|---|---|---|
| AZT | 12 | 2/12 | $2.2 \times 10^{-4}$ |
| DDI | 19 | 4/19 | $4.4 \times 10^{-4}$ |
| DDC | 17 | 2/17 | $2.2 \times 10^{-4}$ |
| D4T | 63 | 23/63 | $2.5 \times 10^{-3}$ |
| Control | 9050 | 0/15 | 0 |

*Concentrations of the antiviral agents were as follows: AZT, 10 uM; DDI, 50 uM; DDC, 10 uM; and D4T, 50 uM.

Table 7. Infection of Jurkat JE6.1 cell clones sensitive and resistant to D4T.

TABLE 7

Infection of Jurkat cell clones Sensitive and Resistant to D4T*

| Clone** | No Drug | 50 uM D4T | 100 uM D4T |
|---|---|---|---|
| Bulk | ++++ | ++ | + |
| R1 | ++++ | ++++ | ++++ |
| R3 | ++++ | +++ | ++ |
| R4 | ++++ | − | − |
| R7 | ++++ | − | − |
| R12 | ++++ | ++++ | ++++ |
| R14 | ++++ | + | − |
| R15 | ++++ | ++++ | ++++ |

TABLE 7-continued

Infection of Jurkat cell clones Sensitive and Resistant to D4T*

| Clone** | No Drug | 50 uM D4T | 100 uM D4T |
|---------|---------|-----------|------------|
| R16 | ++++ | + | − |
| R19 | ++++ | − | − |
| R20 | ++++ | ++++ | +++ |
| R21 | ++++ | ++++ | ++++ |
| R22 | ++++ | ++ | + |
| R26 | ++++ | + | − |
| R29 | ++++ | − | − |
| R33 | ++++ | +++ | + |
| R36 | ++++ | ++++ | ++ |
| C2 | ++++ | − | − |
| C23 | ++++ | − | − |
| C26 | ++++ | − | − |
| C27 | ++++ | − | − |
| JE6.1 | ++++ | − | − |

These data represent the percentage of cells infected with MLV-LacZ in the presence of D4T in comparison with cells infected in the absence of D4T ([% cell infected in the presence of D4T/% cell infected in the absence of D4T]× 100).

* (−), 20%; (+) 21–40%; (++) 41–60%; (+++), 61–80%; (++++), 81–100%.
** Bulk=bulk culture; R=resistant clone; C=control clone; JE6.1=parental cell line.

Table 8. Jurkat JE6.1 cells refractory to the antiviral activity of d4T (D4T bulk, D4TR1, D4TR3) and control JE6.1 cells were infected with HIV-IIIB in the presence of 0.001 uM d4T, 0.01 uM d4T 0.1 uM d4T, 1 uM d4T, 10 uM d4T, 100 uM d4T and 1000 uM d4T in the presence of 0.005 uM FUdr, 0.01 uM FUdr or 0.25 uM FUdr. The IC50 represents the concentration of D4T required for 50% inhibition of RT activity on day 6 of infection.

TABLE 8

AZT/FUdr Susceptibility in Cells Sensitive and Refractory to the Antiretroviral Activity of D4T

| | JE6.1 $IC_{50}$ Sensitivity | | D4TBulk $IC_{50}$ Sensitivity | | D4TR1 $IC_{50}$ Sensitivity | | D4TR3 $IC_{50}$ Sensitivity | |
|---|---|---|---|---|---|---|---|---|
| Treatment | (uM) | (fold) | (uM) | (fold) | (uM) | (fold) | (uM) | (fold) |
| D4T | 0.02 | — | 3 | — | 74 | — | 2 | — |
| D4T + 0.005F | 0.003 | 3 | 0.8 | 4 | 0.9 | 82 | 0.1 | 20 |
| D4T + 0.01F | 0.001 | 20 | 0.04 | 75 | 0.2 | 370 | 0.03 | 67 |
| D4T + 0.025F | 0.0008 | 25 | 0.009 | 333 | 0.01 | 7400 | 0.007 | 286 |

References

1. Avramis, V. I; Kwock, R.; Solorzano, M. M.; Gomperts, E. Evidence of in vitro development of drug resistance to azidothymidine in T-lymphocytic leukemia cell lines (Jurkat E6–1/AZT-100) and in pediatric patients with HIV-1 infection. Acquir Immune Defic Syndr 1993 6:1287–96.
2. Boucher, C. A., Lange, J. M., Miedema, F. F., et al. HIV-1 biological phenotype and the development of zidovudine resistance in relation to disease progression in asymptomatic individuals during treatment. AIDS 1992;6:12591264.
3. Bradshaw, H. D. and P. L. Deininger. 1984. Human thymidine kinase gene: molecular cloning and nucleotide sequence of a cDNA expressible in mammalian cells. Mol. Cell. Biol 4:2316–2320.
4. Chomozynski, P. and Sacchi, N. 1987. Single-step method of RNA isolation by acid guanidinium thiocyanate-phenol-chloroform extraction. Anal. Biochem. 162:156–159.
5. Fischl, M. A., Richman, D. D., Grieco, M. H., et al. The efficacy of azidothymidine AZT in the treatment of patients with AIDS and the AIDS related complex. A double blind placebo controlled trial. N. Engl. J. Med. 1987;317:185–191.
6. Gao W-Y, Shirasaka T., Johns, D. G., Broder, S., Mitsuya, H. Differential phosphorylation of azidothymidine, dideoxycytidine and dideoxyinosine in resting and activated peripheral blood mononuclear cells. J. Clin. Invest. 1993;91 :2326–2333.
7. Johnston, M. I., McGowan, J. J. Strategies and Progress in the Development of Antiretroviral Agents. In: DeVita VT, Hellman S, Rosenberg SA, ed. AIDS: Etiology, Diagnosis, Treatment and Prevention. Philadelphia: J. B. Lipincott Company, 1992: 357–372.
8. Larder, B. A., Coates, K. E., Kemp, S. D. Zidovudine-resistant human immunodeficiency virus selected by passage in cell culture. J. Virol. 1991: 65:5232–5236.
9. Larder, B. A., Darby, G., Richman, D. D. HIV with reduced sensitivity to zidovudine (AZT) isolated during prolonged therapy. Science 1989;243:17311734.
10. Lee, L-S. and Y-C. Cheng. 1976. Human deoxythymidine kinase. J. Biol. Chem. 251: 2600–2604.
11. Mayers, D. L. Clinical significance of in vitro zidovudine resistance. Third Workshop on Viral Resistance. Gaithersburg, Maryland: 1993.
12. Mayers, D. L., McCutchan, F. E., Sanders, B. E., et al. Characterization of HIV isolates arising after prolonged zidovudine therapy. J Acquir Immune Defic Syndr 1992;5 (8):749–59.
13. Mellors, J., Dutschman, G., Im, G., Tramontano, E., Winkler, S. R., Cheng, Y. C. In vitro selection and molecular characterization of HIV-1 resistant to non-nucleoside inhibitors of reverse transcriptase. Mol. Pharmacol. 1992;41:446451.
14. Mosmann, T. Rapid calorimetric assay for cellular growth and survival: application to proliferation and cytotoxicity assays. J Immunol Methods 1983 65: 55–63.
15. Mukherji, E., Au, J. L. S., Mathes, L. E. Differential antiviral activities and intracellular metabolism of 3'-azido-3'-deoxythymidine and 2', 3'-dideoxyinosine in human cells. Antimicrob. Agents Chemother. 1994, 38:1573–1579.
16. Nunberg, J. H., Schleif, W. A., Boots, E. J., et al. Viral resistance to to HIV-1 specific pyridinone reverse transcriptase inhibitors. J. Virol. 1991;65:4887–92.
17. Nyce, J., Leonard, S., Canupp, D., Schulz, S., Wong, S. Epigenetic mechanisms of drug resistance: Drug induced 17. DNA hypermethylation and drug resistance. Proc. Natl. Acad. Sci. 1993;90:2960–2964.
18. Page, K. A., Landau, N., Littman, D. R. Construction and use of a human immunodeficiency virus vector for analysis of of viral infectivity. J. Virol. 1990,34:5270–5276.
19. Richman, D. D., Fischl, M. A., Grieco. M. H., et al. The toxicity of azidothymidine in the treatment of patients with AIDS and AIDS-related complex: A double blind placebo controlled study. N. Engl. J. Med. 1987;322:941.
20. Richman, D. D. Antiretroviral Therapy: Azidothymidine and Other Deoxynucleoside Analogues. In: DeVita VT, Hellman S, Rosenberg SA, ed. AIDS: Etiology, Diagnosis, Treatment and Prevention. Philadelphia: J. B. Lippincott, 1992: 373–387.
21. Richman, D. D., Grimes, J. M., Lagakos, S. W. Effect of stage of disease and drug dose on zidovudine susceptibilities of isolates of human immunodeficiency virus. J. Acquired Immune Defic. Syndr. 1990;3:743–746.
22. Richman, D., Shih, C. K., Lowy, I., et al. Human immunodeficiency virus type 1 mutants resistant to non-nucleoside inhibitors of reverse transcriptase arise in tissue culture. Proc Natl Acad Sci U.S.A 1991; 88 (24):11241–5.
23. Saag, M. S., Emini, E. A., Laskin, O. L. A short terrn clinical evaluation of L697,661, a non-nucleoside inhibitor of HIV-1 reverse transcriptase. N. Engl. J. Med. 1993;329: 1065–1072.
24. Sherley, J. L. and T. J. Kelly. 1988. Human cytosolic thymidine kinase. J. Biol. Chem. 263:375–382.
25. Spector, S. A., Kennedy, C., McCutchan, J. A. The antiviral effect of zidovudine and and ribavirin in clinical trials and the use of p24 antigen as a virologic marker. J. Infect. Dis. 1989;159:822.
26. Strair, R. K., Medina, D. J., Nelson, C. J., Graubert, T., Mellors, J. W. Recombinant retroviral systems for the analysis of drug-resistant HIV. Nucl. Acids Res. 1993; 21:4836–42.
27. Strair, R. K., Nelson, C. J., Mellors, J. W. Use of recombinant retroviruses to characterize the activity of antiretroviral compounds. J. Virol. 1991;65:63396342.
28. Wei, X., Ghosh, S. K., Taylor, M. V., Johnson, V. A., Emini, E. A., Deutsh, P., Lifson, J. D., Bonhoeffer, S. Nowak, M. A., Hahn, B. H., Saag, M. S., Shaw, G. M. (1995) Nature 373:117.
29. Loveday, C., Kaye, S., Tenant-Flowers, M., Semple, M., Ayliffe, U., Weller, I. D., Tedder, R. S. (1995) Lancet 345:820–825.
30. Ho, D. D., Neumann, A. U., Chen, W.-, Leonard, J. M., Markowitz, M. (1995) Nature 373:123–126.
31. Medina, D. J., Tung, P. P., Lerner-Tung, M. B., Nelson, C. J., Mellors, J. W., Strair, R. K. (1995) J. Virol. 69:1606–1611.
32. Haertle, T., Carrera, C. J., Wasson, D. B., Sowers, L. C., Richman, D. D., Carson, D. A. (1988) J. Biol. Chem. 262:5870–5875.
33. Reed,L., and Muench, H. (1938) Am. J. Hyg. 27:493–496.
34. Antoni, B. A., Sabbatini, P., Rabson, A. B., While, E. (1995) J. Virol. 69:2384–2392.
35. Medina, D. J., P. P. Tung, B. Sathya, and R. K. Strair. 1996. Use of floxuridine to modulate the antiviral activity of zidovudine. AIDS Res. Hum. Retroviruses. 12:965–968.
36. Miller, A. D., and G. T. Rosman. 1989. Improved retroviral vectors for gene transfer and expression. Biotechniques. 7:980–990.
37. Willey, R. L., D. H. Smith, L. A. Lasky, T. S. Theodore, P. L. Earl, P. Moss, D. J. Caponi, and M. A. Martin. 1988. In vitro mutagenesis identifies a region within the envelope gene of the human immunodeficiency virus that is critical for infectivity. J. Virol. 62:139–147.
38. Havlir, D., S. Eastman, and D. D. Richman. 1995. HIV-1 kinetics: Rates of production and clearance of viral populations in asymptomatic patients treated with nevirapine. 2nd Natl. Conf. on human Retroviruses and Related Infections. Washington D.C. January 1995. Abstract 229.
39. Gulick, R., J. Mellors, D. Havlir, J. Eron, et al. 1996. Safety and activity of indinavir in combination with zidovudine and lamivudine. 3rd Natl. Conf. on Human retroviruses and related infections. Washington D.C. January 1996.
40. Zhang, H., O. Bagasra, M. Nikura, B. J. Poiesz, and R. J. Pomerantz. 1994. Intravirion reverse transcripts in the peripheral blood plasma of human immunodeficiency virus type-1 infected individuals. J. Virol. 68:7591–7597.
41. Ahluwalia, G. A., W. Gao, H. Mitsuya, and D. G. Johns. 1996. 2,3'-didehydro-3'-deoxythymidine: Regulation of its metabolic activation by modulators of thymidine-5'-triphosphate biosynthesis. Mol. Pharm. 50:160–165.
42. Havlir D., and D. D. Richman. 1994. Viral dynamics of HIV: Implications for drug develpoment and therapeutic strategies. Ann. Int. Med. 124:984–989.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:
1. A method for treating a human with human immunodeficiency virus infection which comprises administering to the human a synergistic therapeutic combination of a therapeutically effective amount of a 3'-azido-3'-deoxythymidine, and floxuridine, or pharmaceutically acceptable salts thereof.
2. The method according to claim 1, further comprising a therapeutically effective amount of a folate antagonist, or pharmaceutically acceptable salt thereof.
3. The method according to claim 1, further comprising a therapeutically effective amount of hydroxyurea, or a pharmaceutically acceptable salt thereof.
4. The method according to claim 1, wherein the 3'-azido-3'-deoxythymidine is administered in an amount from about 5 mg to 250 mg per kilogram body weight per day.
5. The method according to claim 1, wherein the floxuridine is administered in an amount from about 0.01 mg to 25 mg per kilogram body weight per day.
6. The method according to claim 2, wherein the folate antagonist is administered in an amount from about 0.05 mg to 25 mg per kilogram body weight per day.
7. The method according to claim 6, wherein the folate antagonist is administered in an amount from about 0.05 mg to 10 mg per kilogram body weight per day.
8. The method according to claim 2, wherein the folate antagonist is selected from the group consisting of methotrexate and trimetraexate.
9. The method according to claim 2, wherein the folate antagonist is methotrexate.
10. The method according to claim 3, wherein the hydroxyurea is administered in an amount from about 5 mg to 250 mg per kilogram body weight per day.
11. The method according to claim 10, wherein the hydroxyurea is administered in an amount from about 7.5 mg to 100 mg per kilogram body weight per day.

* * * * *